United States Patent
Zagrai et al.

(10) Patent No.: US 8,671,761 B2
(45) Date of Patent: Mar. 18, 2014

(54) METHOD OF ASSESSING BOLTED JOINT INTEGRITY

(75) Inventors: Andrei Zagrai, Socorro, NM (US); Derek Doyle, Albuquerque, NM (US)

(73) Assignee: New Mexico Technical Research Foundation, Socorro, NM (US)

( * ) Notice: Subject to any disclaimer, the term of this patent is extended or adjusted under 35 U.S.C. 154(b) by 535 days.

(21) Appl. No.: 12/968,144

(22) Filed: Dec. 14, 2010

(65) Prior Publication Data

US 2011/0138918 A1   Jun. 16, 2011

Related U.S. Application Data

(60) Provisional application No. 61/286,248, filed on Dec. 14, 2009.

(51) Int. Cl.
*G01N 29/07* (2006.01)
*G01N 29/11* (2006.01)
*G01N 29/48* (2006.01)

(52) U.S. Cl.
USPC ............... 73/598; 73/597; 73/599; 73/600; 73/761

(58) Field of Classification Search
USPC ........... 73/602, 620, 622, 761, 597, 598, 599, 73/600
See application file for complete search history.

(56) References Cited

U.S. PATENT DOCUMENTS

| | | | |
|---|---|---|---|
| 3,918,294 A | 11/1975 | Makino et al. | |
| 4,062,229 A | 12/1977 | Godfrey et al. | |
| 4,198,865 A | 4/1980 | Tarpley, Jr. et al. | |
| 4,413,518 A | 11/1983 | Jones | |
| 4,549,437 A | 10/1985 | Weins et al. | |
| 4,602,511 A | 7/1986 | Holt | |
| 5,948,984 A | 9/1999 | Hedberg | |
| 7,152,475 B2 | 12/2006 | Nakamura | |
| 7,360,435 B2 | 4/2008 | Nassar et al. | |
| 2004/0255678 A1* | 12/2004 | Nagashima et al. | 73/620 |
| 2005/0178205 A1 | 8/2005 | Nitsan | |
| 2007/0056375 A1* | 3/2007 | Akdeniz et al. | 73/649 |

* cited by examiner

*Primary Examiner* — Peter Macchiarolo
*Assistant Examiner* — Rose M Miller
(74) *Attorney, Agent, or Firm* — Robert W. Becker; Berenbaum Weinshienk PC

(57) ABSTRACT

A method of assessing bolted joint integrity. A guided wave is sent through a structure containing at least one bolted joint. The guided wave that is subsequently propagated through the structure and interacted with the bolted joint is measured to obtain a measured result. At least one parameter of the guided wave after its travel through the structure, and after having been affected by a nonlinear acoustic behavior of the bolted joint, is analyzed. Either at least one guided wave parameter is compared to a wave propagation pattern of the bolted joint at a correct torque level, or variation of at least one guided wave parameter is compared, to determine changes in wave propagation time and/or wave propagation shape. An incorrect torque level of the bolted joint is inferred from any changes that are determined.

9 Claims, 26 Drawing Sheets

METHOD OF ASSESSING BOLTED JOINT INTEGRITY

The instant application should be granted the priority date of Dec. 14, 2009, the filing date of the corresponding U.S. provisional patent application 61/286,248.

BACKGROUND OF THE INVENTION

The present invention relates to a method for assessing bolted joint integrity.

It is desirable to be able to assess whether or not the torque level of bolts of a bolted joint assembly is correct, and also to be able to locate damaged and/or loose bolts. In this regard, it is furthermore desirable to utilize torque measurement techniques based on elastic wave propagation that is not introduced directly into the bolt itself, as has been done in the past.

It is therefore an object of the present application to realize the aforementioned tasks, and in particular in an improved manner.

BRIEF DESCRIPTION OF THE DRAWINGS

This object, and other objects and advantages of the present application, will appear more clearly from the following specification in conjunction with the accompanying schematic drawings, in which:

FIG. 2b is an enlarged view of the portion labeled FIG. 2b in FIG. 2a;

FIG. 19b shows the power spectrums of time-domain records in FIG. 19a;

SUMMARY OF THE INVENTION

Figure 1:
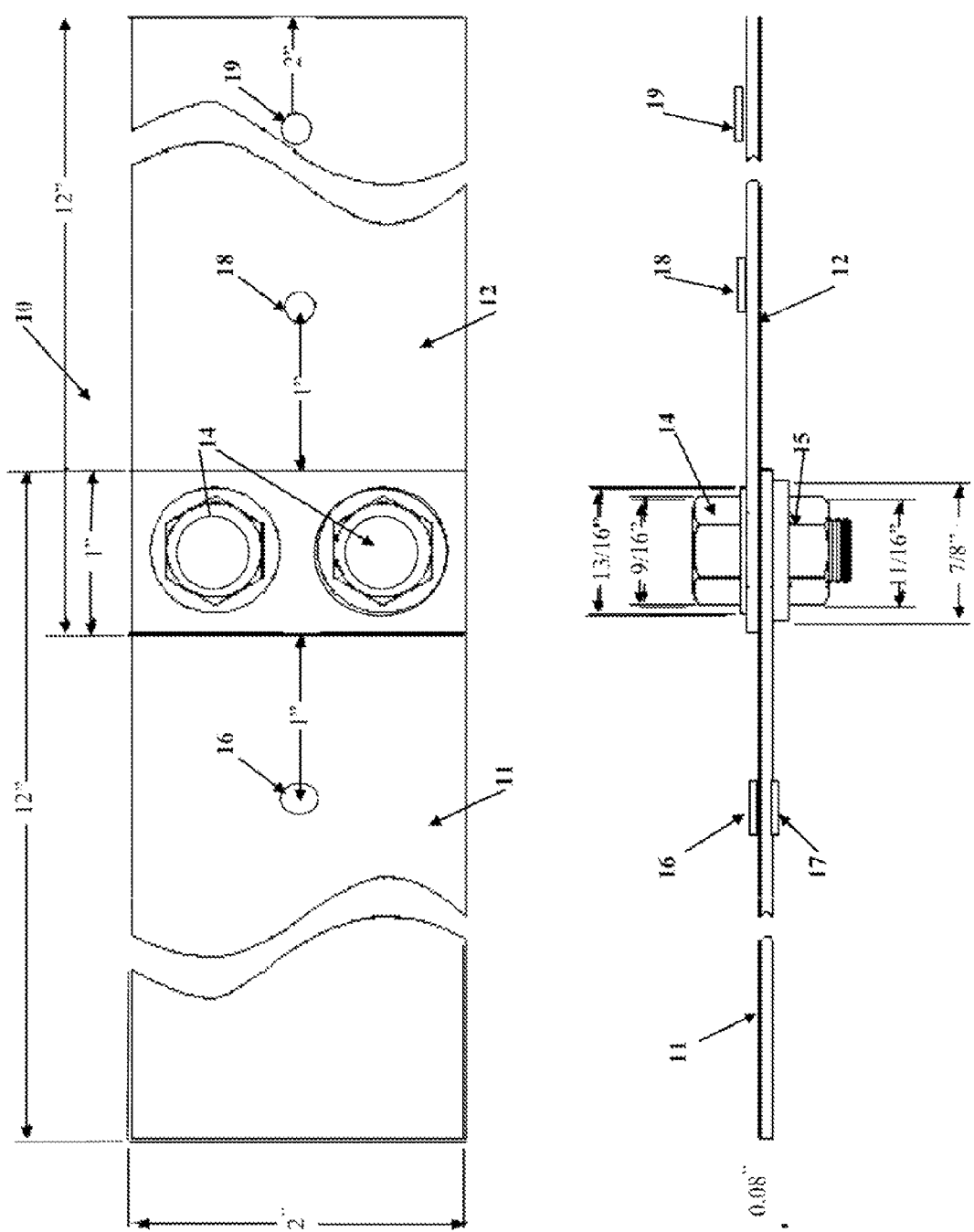
FIG. 1 shows a bolted joint assembly structure with sensors.

The present application defines a method of assessing bolted joint integrity by sending a guided wave through a structure that contains at least one bolted joint; measuring the guided wave that has subsequently propagated through the structure and interacted with the at least one bolted joint to thus obtain a measured result; analyzing at least one parameter of the measured result of the guided wave after its travel through the structure and after having been affected by nonlinear acoustic behavior of the at least one bolted joint; either comparing at least one guided wave parameter to a wave propagation pattern of the at least one bolted joint at a correct torque level, or comparing variation of at least one guided wave parameter to determine changes in at least one of wave propagation time and wave propagation shape; and inferring from any changes that are determined an incorrect torque level of the at least one bolted joint.

A bolt exerts a compressive stress on a structural element and therefore the sound speed of the elastic wave in a structure will change depending on the value of torque applied to the bolt. This is known as a nonlinear acoustic-elastic effect. Hence, estimation of the torque can be obtained by measuring delays in propagation of short pulses of elastic waves in structural elements. Applicants' method utilizes changes in the propagation time and/or in the shape of the propagating guided elastic wave for inferring information on the torque level applied on the bolted joint assembly. These changes can also be utilized to locate loosened bolts. In particular, the changes indicated are associated with the torque-induced nonlinear characteristics of the wave propagation path through the joint.

Applicants' method allows for an efficient and rapid diagnosis of structural bolted joint assemblies. The availability of information on bolted joint integrity can lead directly to a number of benefits, including, but not limited to, preventing structural deterioration, unexpected system behavior and structural failure; extending operational life of existing structures and structural repairs, for example in connection with bridges and the like; opportunities to avoid overdesigning a structure, thus allowing for a reduction in weight, for example in connection with aircraft and other vehicles, thus enhancing their cargo-carrying ability; optimization of structural behavior, which leads to an improvement of operation efficiency and performance; and structural condition assessment during, or immediately after, an emergency situation. Applicants' method is applicable to any structure, system or element that incorporates bolted joints and allows for generation and propagation of guided waves, such as, but not limited to, space structures, including satellites and spaceships, aeronautical structures, including airplanes and helicopters, ground vehicles, navy ships and submarines, mechanical assemblies, including engines, motors and the like, civil structures, including buildings and bridges and other elements of infrastructure.

Further specific features of the present application will be described in detail subsequently.

DESCRIPTION OF SPECIFIC EMBODIMENTS

The present invention discloses a method of assessing bolted joint integrity, such as of the bolted joint assembly illustrated in FIG. 1. The structure 10 shown here is composed of two beams 11 and 12, such as two aluminum 2024 beams that are 12 inches in length, 2 inches in width and 0.08 inches in thickness. In the illustrated bolted joint assembly structure 10, the two beams 11 and 12 are connected to one another by two screws 14, such as two ⅜-16, grade 8, hex flange, 1 inch steel screws, along with ⅜-16 UNC flange nuts 15.

Four preferably permanently installed or embedded sensors 16, 17, 18 and 19, such as piezoelectric active sensors fabricated from APC 850 piezoelectric ceramic having a 7 mm diameter and a thickness 0.2 mm, were positioned on the beams 11 and 12 as shown in FIGS. 1a and 1b. The sensors 16-19 can be bonded to the beams 11 and 12, for example by means of a cyanoacrylate adhesive.

Figure 2A:
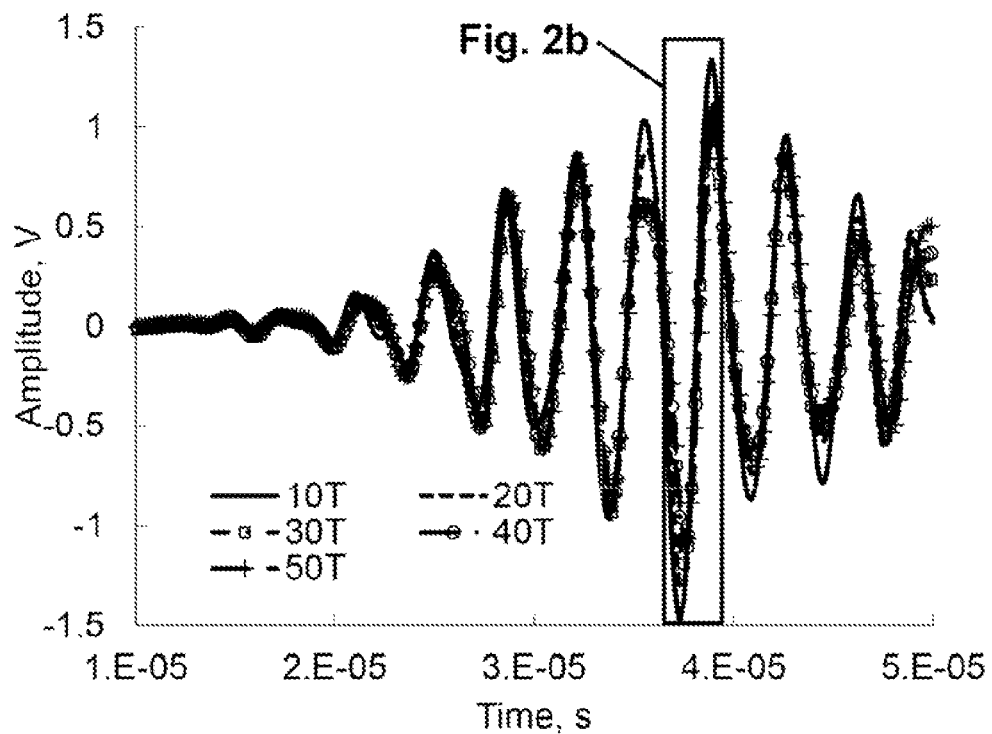
FIG. 2a is a recordation of guided wave signals at different levels of applied torque.
Figure 2B:
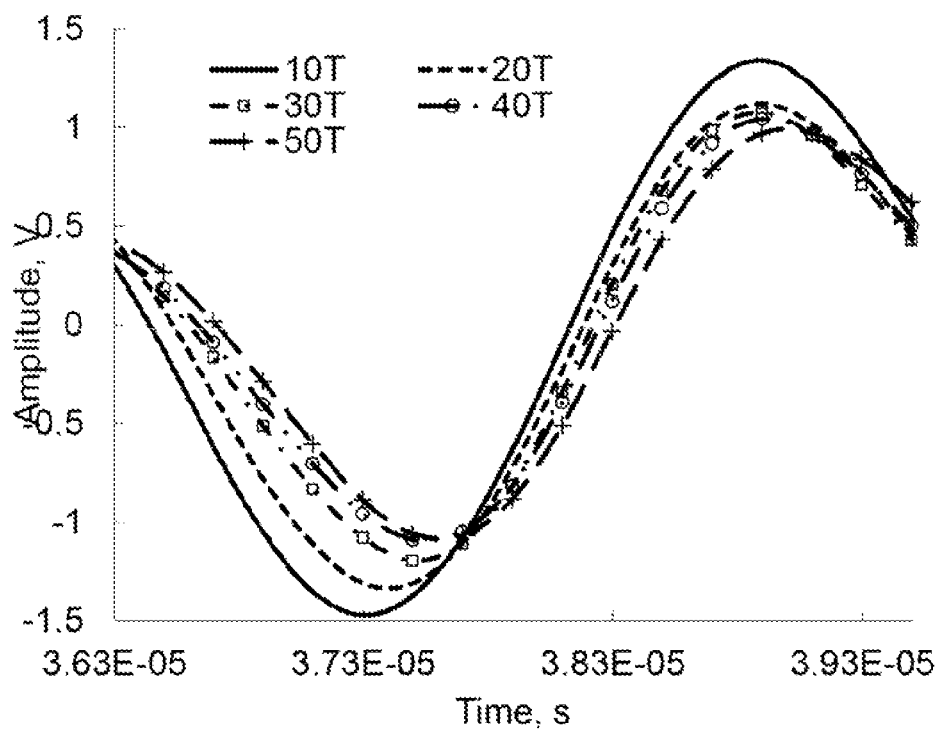

In one test sequence, some of the piezoelectric active sensors were excited with a 4 count 270 kHz pulse provided by a signal generator. The test procedure was as follows: a 10 ft-lbs torque was initially applied to both of the bolts 14. The bolted joint assembly structure 10 was placed on foam, and an input signal was supplied to the sensor 16. The elastic wave travelled through the structure 10, i.e. through the beam 11, the area of the bolted joint, and the beam 12, and was measured with the sensor 18. The same procedure was repeated at increased torque increments of 10 ft-lbs until 50 ft-lbs was reached. This resulted in five data records, namely for 10, 20, 30, 40 and 50 ft-lbs respectively. An example for the five levels of torque is shown in FIGS. 2a and 2b, with FIG. 2b being an enlarged view of the segment depicted within the rectangle in FIG. 2a. With regard to the use of the various sensors, it should be noted that the input signal could be applied to any of the sensors 16-19, and the measurements could also be taken with any of the sensors. The critical point is that the acoustic wave propagate through the joint, i.e., interact with the joint. It would also be possible to transmit and measure with the same sensor, for example the sensor 16. Furthermore, although measuring with additional sensors 17-19 is not required, doing so would provide additional information, for example with regard to location, improved sensitivity, etc.

The tests showed that the amount of torque applied to the bolts 14 have a noticeable effect on the time of arrival, and the shape of the elastic wave that was propagated through the bolted joint assembly, as can be seen in FIGS. 2a and 2b. In particular, FIGS. 2a and 2b show that increasing the torque results in a pulse delay proportional to the torque level; in addition to the temporal characteristics of the signal, changes in the shape of the waveform can be seen as the torque increases.

Figure 3:
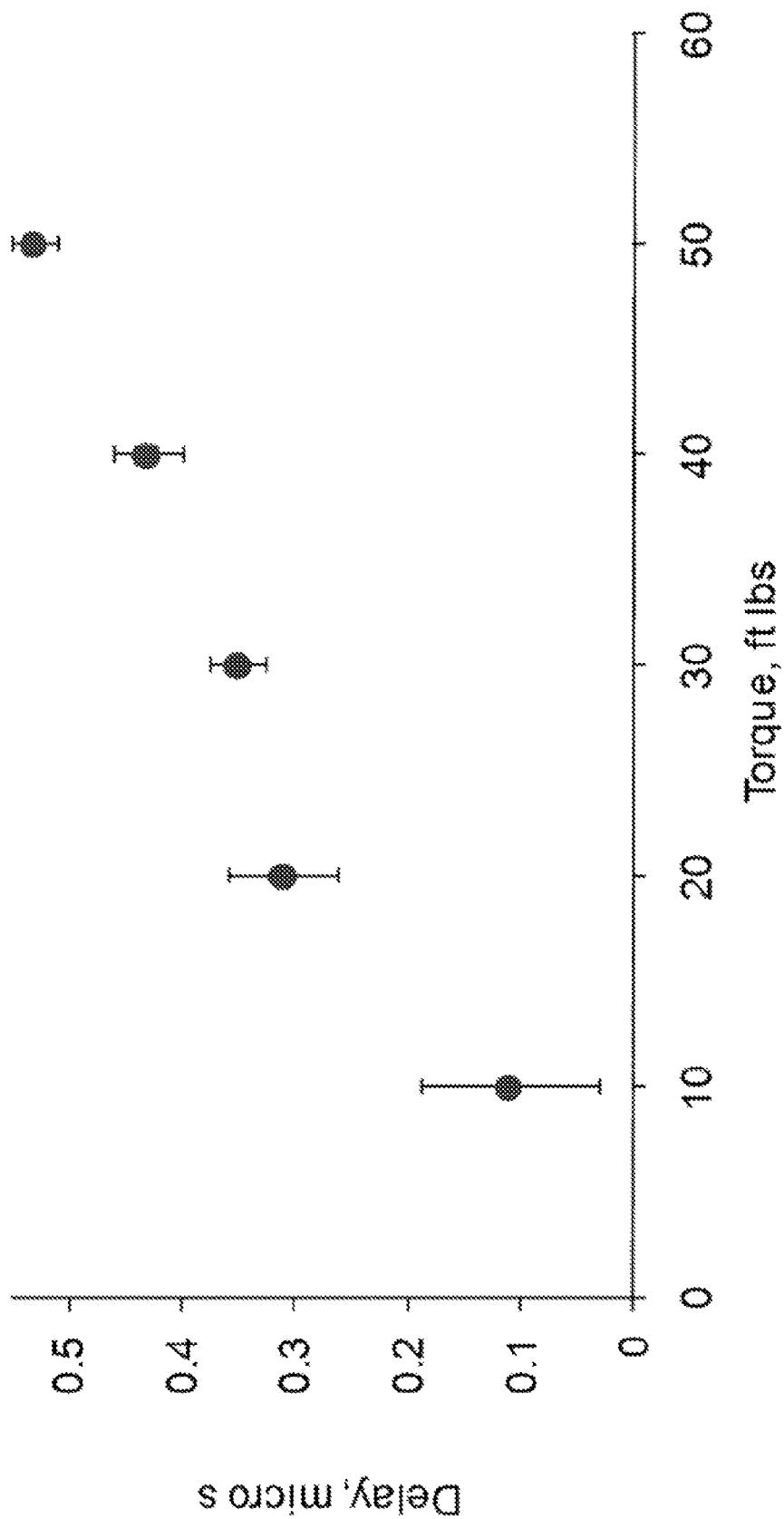
FIG. 3 illustrates the relative delay of the guided wave pulse verses applied torque.

To establish a relationship between the torques applied to the bolts 14, and the respective delays of the signal arrival times, eight measurements were considered for each level of torque. The results are represented in FIG. 3, which shows average values with standard deviation margins. FIG. 3 clearly demonstrates that level of torque applied to a bolted joint assembly can be inferred from a measurement of a pulse delay of the guided elastic wave. This is attributed to nonlinear acousto-elastic effect.

As already mentioned, FIG. 2 indicates that in addition to changes in temporal characteristics of the signal, changes in the waveform's shape are noticeable as the torque increases. One way to evaluate these changes is through time-frequency analysis (spectograms). When spectograms were calculated from signals corresponding to the 10, 20, 30, 40 and 50 ft-lbs torque levels, changes of the waveform resulted in difference in signal amplitude and levels of nonlinear spectral components at 540 kHz (the second harmonic) for a 270 kHz pulse. This demonstrates that changes of the waveform's shape can also be used for evaluation of the torque levels applied to the bolted joint assembly.

Figure 4A:
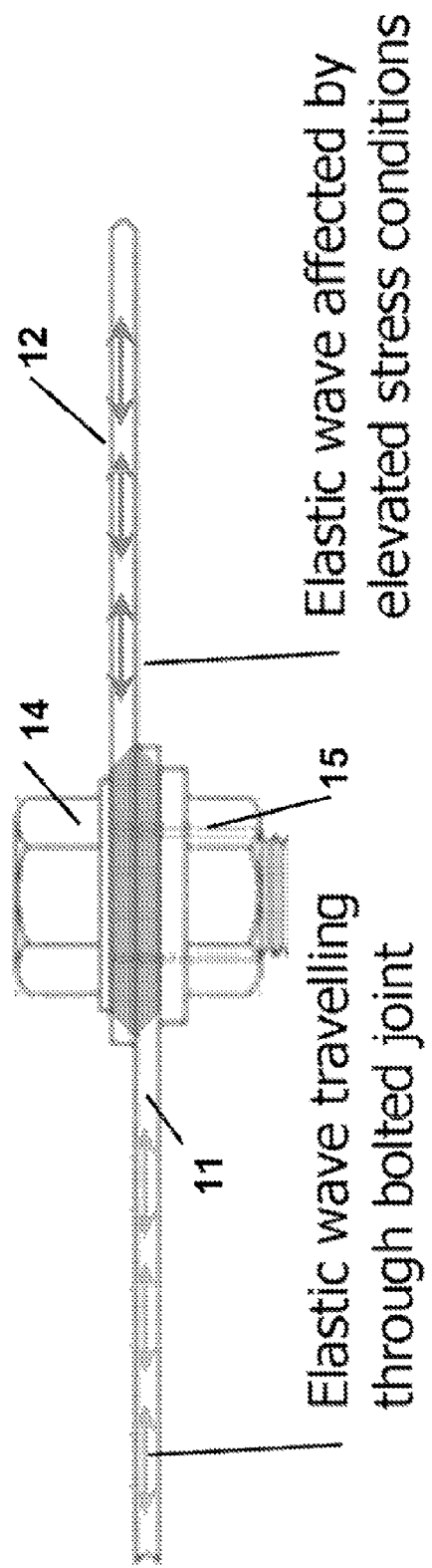
FIG. 4a is a side view showing an exemplary bolted joint geometry.
Figure 4B:
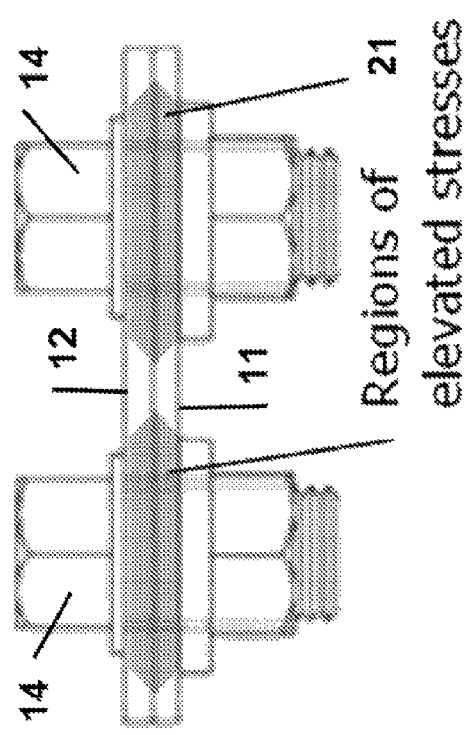
FIG. 4b is a view of the bolts taken transverse to the direction of the wave propagation.

Referring to the bolted joint geometry shown in FIGS. 4a and 4b, shown is a quasi-longitudinal wave propagation in the plates or beams 11 and 12 produced via the bolted joint assembly. It should be noted that although an elastic wave is not strictly longitudinal, since it is a guided $S_0$ mode, at lower frequencies, i.e. a lower kHz range, dispersion may be neglected and the expression for a longitudinal wave in infinite medium is suggested for rough estimation of effect of stress exerted by the bolted joint.

The bolted joint geometry depicted in FIGS. 4a and 4b implies that the material of the beams 11 and 12 is subjected to compressive stress in the regions 21 perpendicular to the direction of the wave propagation. An estimation of the compressive stress can be obtained by considering a force acting on a joint, and the effective area over which the applied force is distributed. An equivalent force applied to a single-bolt joint depends on a torque T, bolt diameter d, and torque coefficient $k_T$ pursuant to the following formula $$F_T = \frac{T}{k_T \cdot d} \tag{1}$$

Coefficient $k_T$ can be calculated from the joint geometry or can be found in handbooks on the bolted joints analysis; using $k_T$=0.2, a bolt diameter d=9.525 mm (⅜ in), and a range of torques from 0 to 70 N·m (from 0 to 50 lbs-ft), an approximate value of 35586 N is obtained for the maximum equivalent force. The area of a joint containing most of the stress can be determined from a pressure-cone method $$A_b = \pi\left(\left(h\tan(\alpha) + \frac{D}{2}\right)^2 - \left(\frac{d}{2}\right)^2\right) \tag{2}$$

where D is the diameter of the washer face and h is the thickness coordinate. For a fixed cone angle a=30°, an estimated $A_b$=343 mm² was obtained. The compressive stress in the joint is calculated as a ratio of $F_T$ and $A_b$. A maximum stress is approximately 100 MPa.

$$\rho c_{ll}^2 = \left(K + \frac{4\mu}{3}\right) + \frac{\sigma}{3K}\left(4K - \frac{8\mu}{3} + \frac{2(K-2\mu/3)^2}{\mu} + \frac{K-2\mu/3}{\mu} \cdot A + \frac{2(K+5\mu/3)}{\mu} \cdot B - 2C\right) \quad (3)$$

Figure 5:
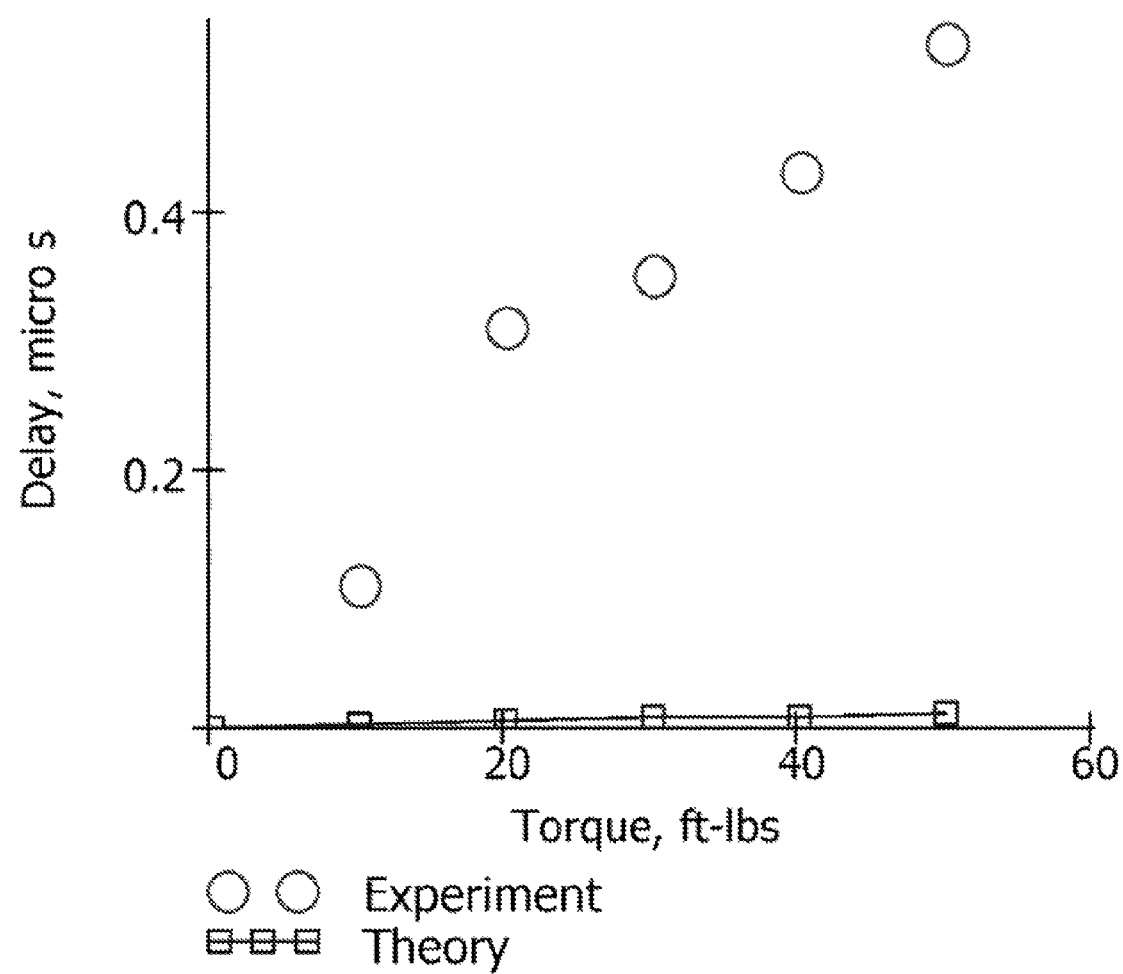
FIG. 5 plots experimental results (circles) and theoretical estimation (blocks) of pulse delay caused by torque applied to a bolted joint assembly.

Equation (3) for the sound speed of a longitudinal in infinite medium, does not describes the present case exactly, but can provide a rough estimate of the sound speed changes due to various static loads. It features two second-order elastic moduli (K and μ) and three third-order nonlinear coefficients A, B, and C. While the second-order constants are widely available for practically all materials, the third-order constants are reported in a limited number of studies. For estimation purposes, data presented by Nagy (2004) for aluminum 7064 was utilized. The numerical values for elastic moduli were calculated from Lame constants and Murnaghan coefficients as follows: K=77.56 GPa, μ=27.4 GPa, A=−403 GPa, B=−195.5 GPa, C=−128.5 GPa, density ρ=2770 kg/m³. Substitution in Equation (3) yields sound speeds ranging from 6418 m/s (no stress) to 6411 m/s (for maximum stress of 100 MPa). These changes of sound speed determine the time delay of the elastic wave. For the specimen used in experimental studies (FIG. 1), the theoretical estimation yielded results presented in FIG. 5. As can be seen from FIG. 5, theory gives approximately one order of magnitude underestimate of the actual delays measured in an experiment. Reasons for such an underestimate may include: (a) difficulties in accurate assessment of compressive stress in the joint, and (b) Equation (3) was developed for the longitudinal wave propagation in infinite, not bonded, medium; the actual speed of a longitudinal wave in a plate is about 1000 m/s lower and will likely result in a more pronounced acousto-elastic effect.

Figure 6:
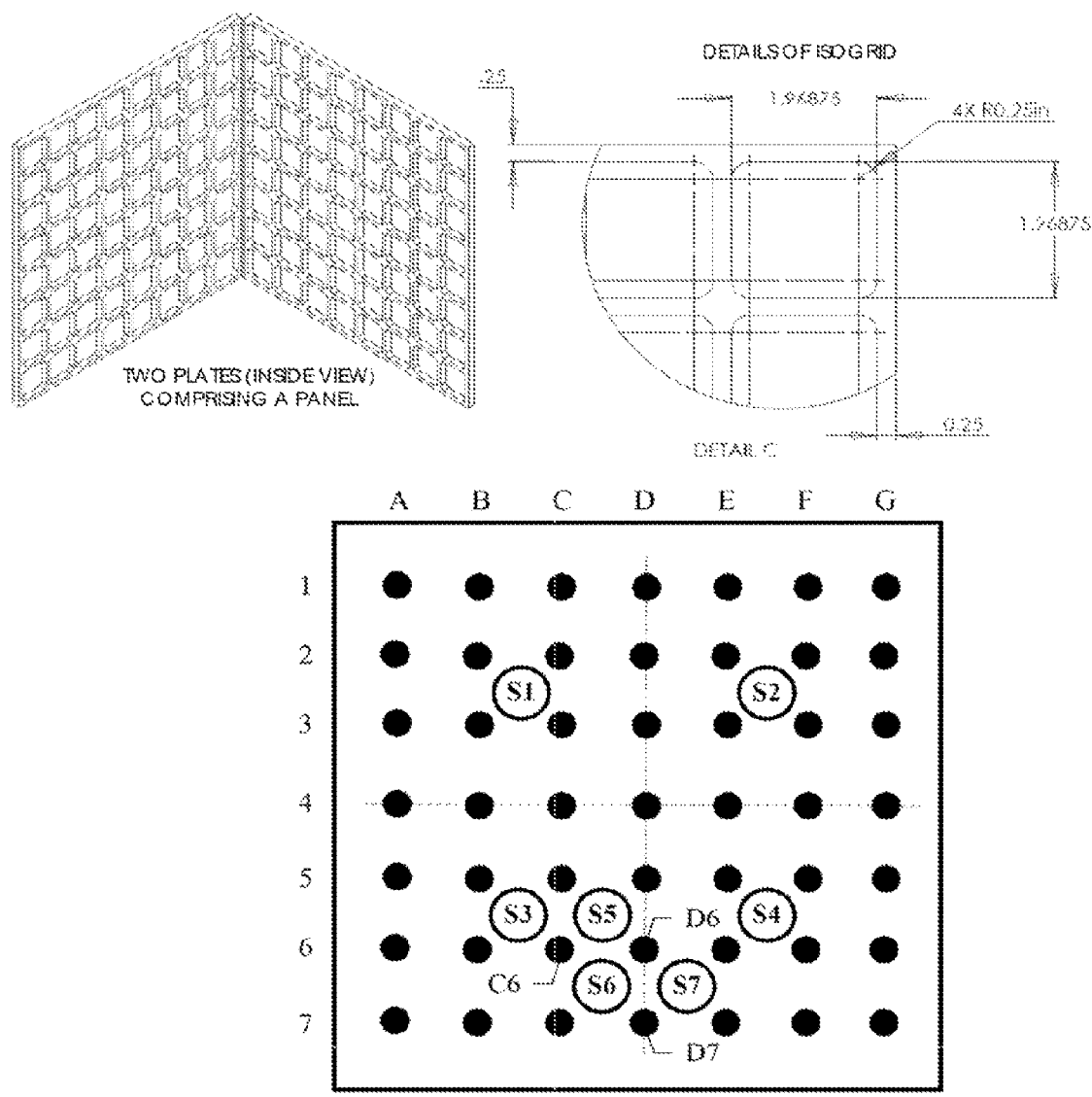
FIG. 6 illustrates a realistic satellite panel comprised of two aluminum plates with iso-grid frames, with the areas of interest being labeled.

To investigate capabilities of the disclosed acousto-elastic method to detect loosened bolts in a practical structure, a complex specimen imitating a basic satellite design was designed. Two aluminum 6061-T6 plates, measuring 18"×18"×0.5", were machined to achieve this goal. The iso-grid frame was made with 64-2"×2"×0.875" cutouts and a 0.25" wall thickness. In the center of each grid junction, a hole was drilled to accommodate a bolt. Each plate contained 49 holes. In the top plate (49) 0.164" through holes with a 0.27" counter bore, 0.164" deep, were machined. The bottom plate featured a similar number of threaded holes for #8-32 bolts but no counter bore. FIG. 6 shows two plates and schematics of bolt locations and initial sensor placement. The bolts used on the panels were 1" long #8-32 socket cap screws. To facilitate referencing, the panel was labeled with a grid layout of A-G× 1-7.

In the acousto-elastic experiment, three piezoelectric active sensors were installed on a surface of the satellite panel between columns C and E and rows 5 and 7. Distance between sensors was set to 2 inches. One sensor (S6) was connected to a RITEC RAM 5000 signal generation unit, while the other sensors (S5 and S7) acted as receivers. In the first step of the experiment, all 49 bolts were tightened with a 9⁄64" hex key. The excitation signal utilized in this test was three count 320 kHz pulse. Illustration of the signal transmitted by S6 to S7 is presented in FIG. 7. The record of the elastic wave signal corresponds to a fully tight condition and a loose bolt at D6. Loose is defined by ⅛ of a full turn (all other bolts are tight). This is just enough for the bolt not to have a force preventing the threads from slipping; i.e. bolt can turn with minimal force.

Figure 7:
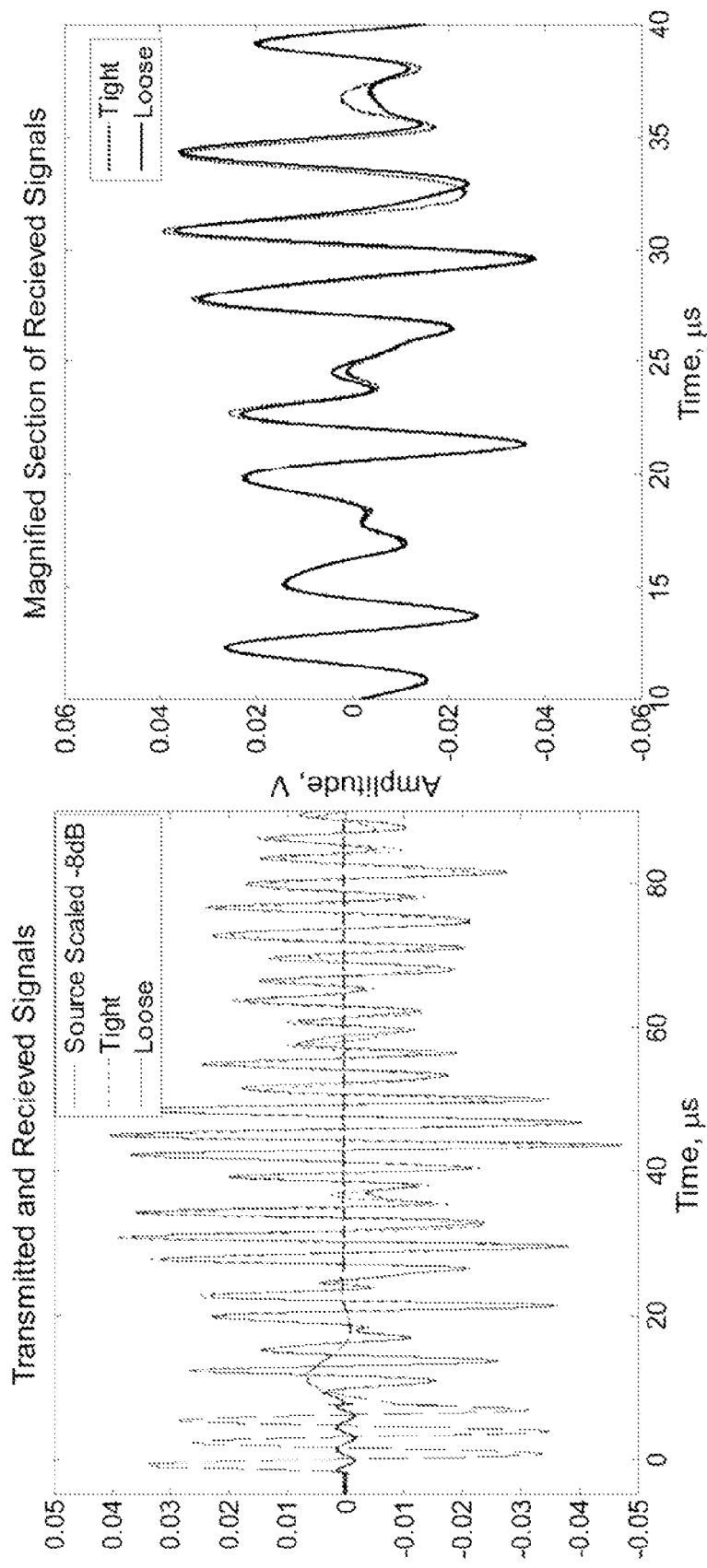
FIG. 7 shows elastic wave signals in the satellite panel experiment, including the transmitted pulse, a tight condition for neighboring bolts, and a loose condition where one bolt is loosened, wherein the lower portion of the drawing indicates phase shifts due to loose and tight test scenarios.

FIG. 7 shows the elastic wave record as an assembly of numerous pulses consisting of primary waves, reflections, and possibly other modes. The repeatable pattern of reflections seen in the figure is likely the result of the structure's iso-grid frame. The first pulse shows practically no difference between tight and loose conditions because the wave propagates through the center of the iso-grid quadrant, which sees very little effect of induced stress. Since the second pulse may correspond to a reflection from the corner, it shows a phase shift for the condition of the loosened bolt. Further shifts are observable in subsequent pulses.

Although previous observations support validity of the damage identification method, it doesn't necessarily mean that the method is effective in locating loose bolts. To investigate this aspect of damage diagnosis, four additional experiments were conducted. Experimental setting for each test is presented in Table 1.

TABLE 1

Experimental setting for diagnosis of the satellite panel

| | Loosened Bolt | | | |
|---|---|---|---|---|
| | D6 | C6 | D6 | C6 |
| Transmitter | S6 | S6 | S6 | S6 |
| Receiver | S5 | S6 | S7 | S7 |

Figure 8A:
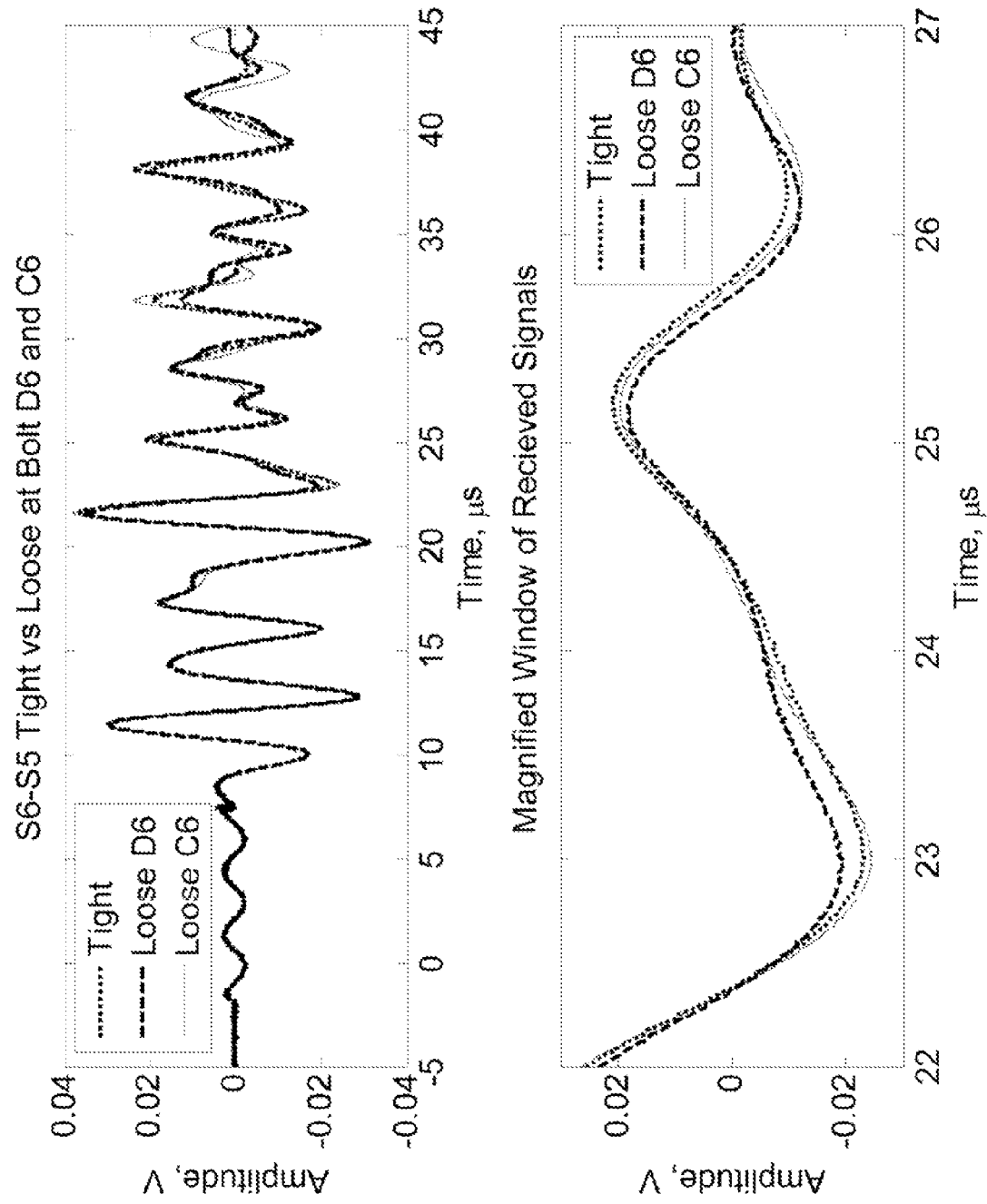
FIGS. 8a & 8b show elastic wave signals in the satellite panel experiment, namely signal reception for the S6-S5 path and the S6-S7 path respectively, in both cases along with zoomed in portions showing where the signal phase shift occurs.
Figure 8B:
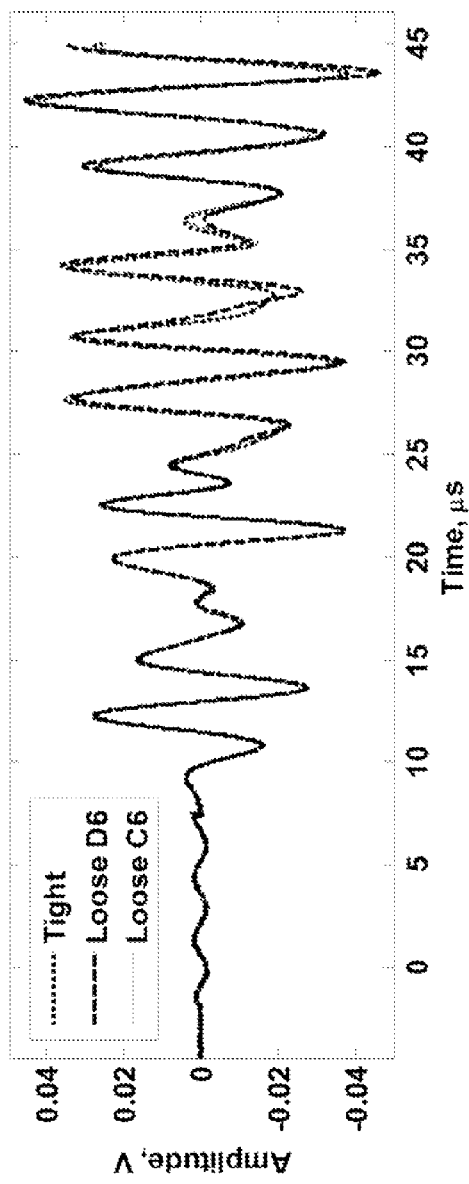
Figure 8B:
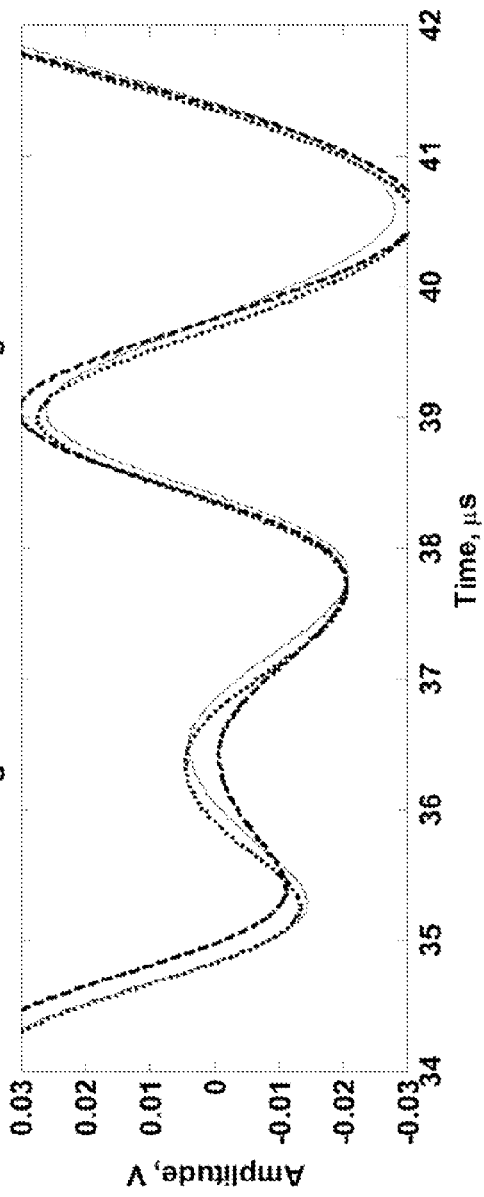

FIGS. 8a and 8b summarize results of the damage location experiments. First, a structural response was measured for a "tight" condition with a sensor pair S5-S6. Then boils C6 and D6 were loosened. Since sensors S5 and S6 are positioned symmetrically with respect to bolts C6 and D6, structural responses having similar features were anticipated. Likewise, the waveform seen is identical to previously reported results. FIG. 8(a) shows that responses for loosened C6 and D6 closely match up to approximately 24 μs. After this time, responses deviate probably due to misalignment of the sensor from the iso-grid centerline. Both responses show features that allow distinguishing of "tight" and "loose" conditions. FIG. 8(b) presents S6-S7 data for the cases when all bolts were tight, bolt C6 was loosened, and bolt D6 was loosened. For this case, bolt C6 is not symmetric with respect to the sensor line and is situated much further away. As a result, in FIG. 8(b) we observe that loosening of D6 causes the difference in responses after the end of the second pulse (also consistent with results depicted in FIG. 9), but loosening of C6 leads to changes noticeable later in the record—after a third pulse. Before 35 μs the data corresponding to loosened C6 show similarity with "tight" condition. Therefore, the conclusion is that by examining the onset of the phase changes in the signal, it is possible to determine location of the loosened bolt.

Figure 9:
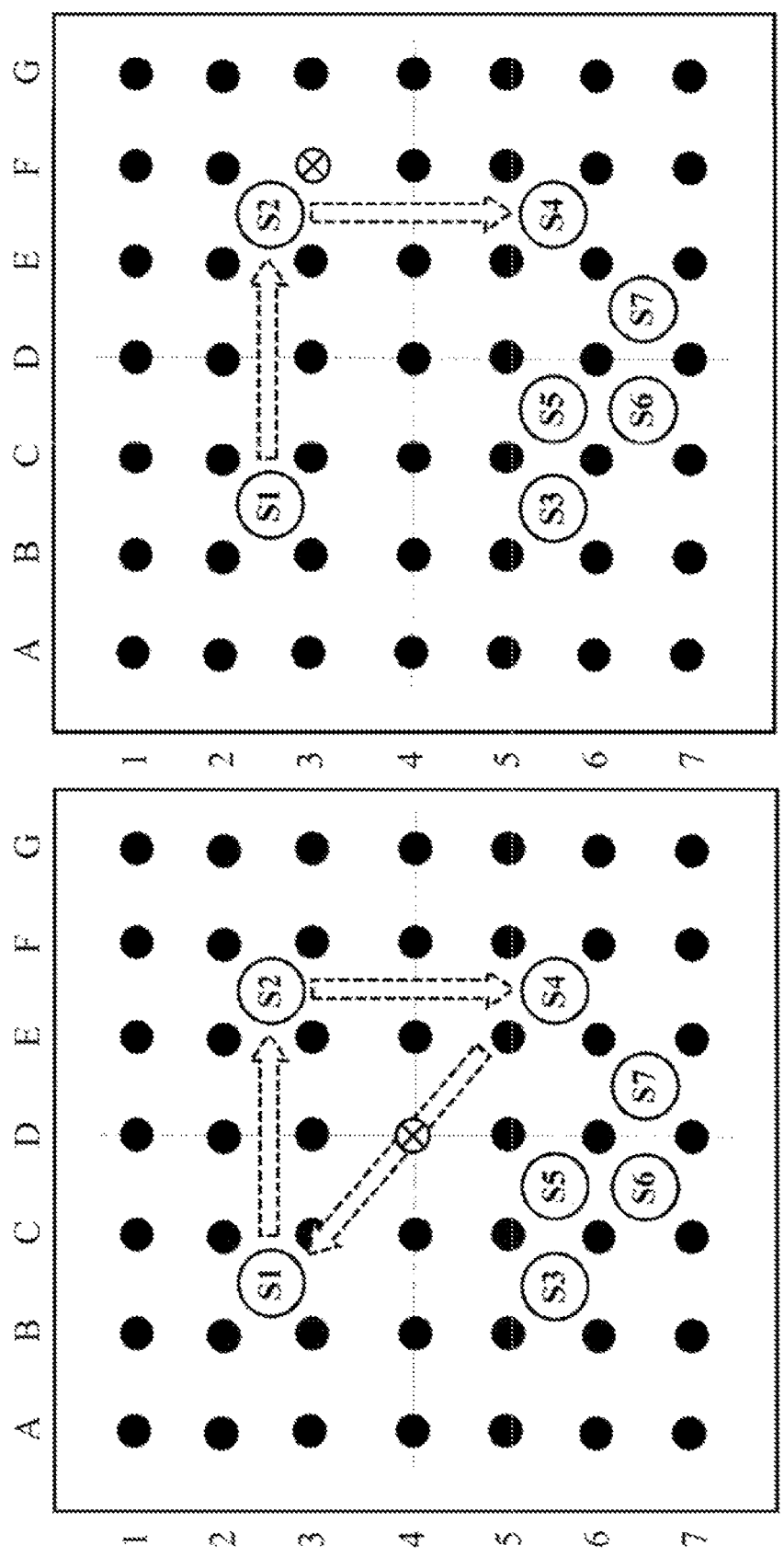
FIG. 9 schematically illustrates the sensor network experiment on a satellite panel, with the arrows indicating wave propagation paths and a loosened bolt (designated by a red dot)

The damage location algorithm described above utilized only few sensors. To imitate realistic damage detection scenarios, an elementary sensor network consisting of four sensors positioned as indicated in FIG. 9 was considered. A set of experiments was considered to determine the effective range of sensors and investigate localization capabilities of the acousto-elastic method. An RT-50 Ohm high power load was attached to the signal out of the RAM 5000 to ensure proper electrical coupling of the signal. The signal was a three count 325 kHz pulse at a transmitting voltage of 20 pp. Scenarios of loose bolts in the quadrant of the transmitting sensor were considered first. Tests were conducted for sensor pairs (Transmitter-Receiver) S3-S4, S2-S4, and S4-S3.

Figure 10:
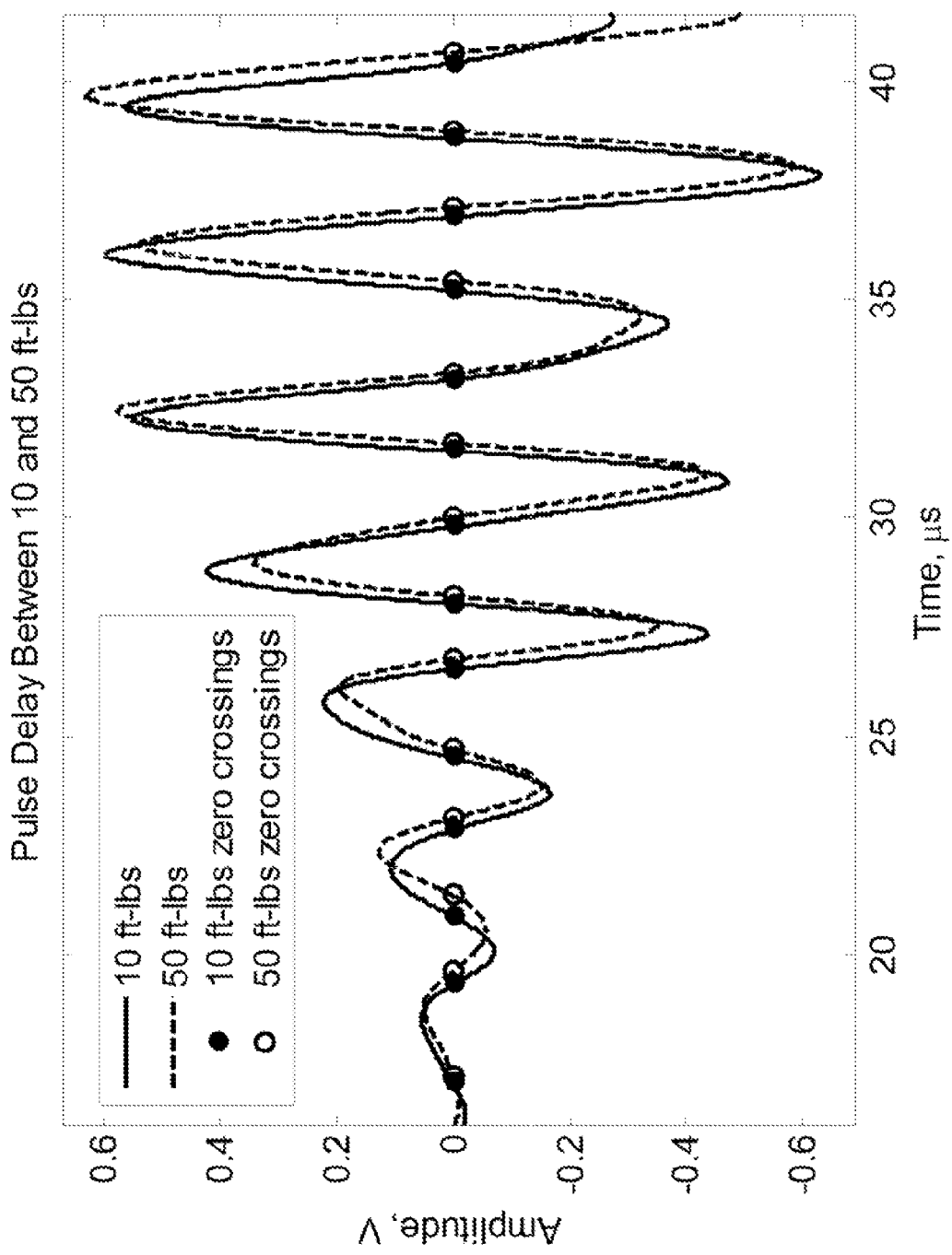
FIG. 10 shows signal responses of 10 ft-lbs and 50 ft-lbs with zero crossing points.

To determine the signal phase change due to a loosened bolt, the zero crossing procedure was developed for analyzing wave propagation paths illustrated in FIG. 9. The procedure can be illustrated using the following example. Two different tests were conducted for bolts D4 and F3 where paths of importance were already known and based on likelihood of giving the best results. A tight condition was recorded for all paths and then the bolt was loosened one fill turn to guarantee phase shift. Zeros crossings were then found for all signals (as illustrated in FIG. 10) and the time difference for zero crossings associated with tight and loose conditions were calculated. As a result, the first significant shift indicated damage location on the time axis. Knowing distance between sensors and sound speed the medium, the position on the time axis can be easily corresponded to actual distance and yield location of the loosened bolt.

Figure 11A:
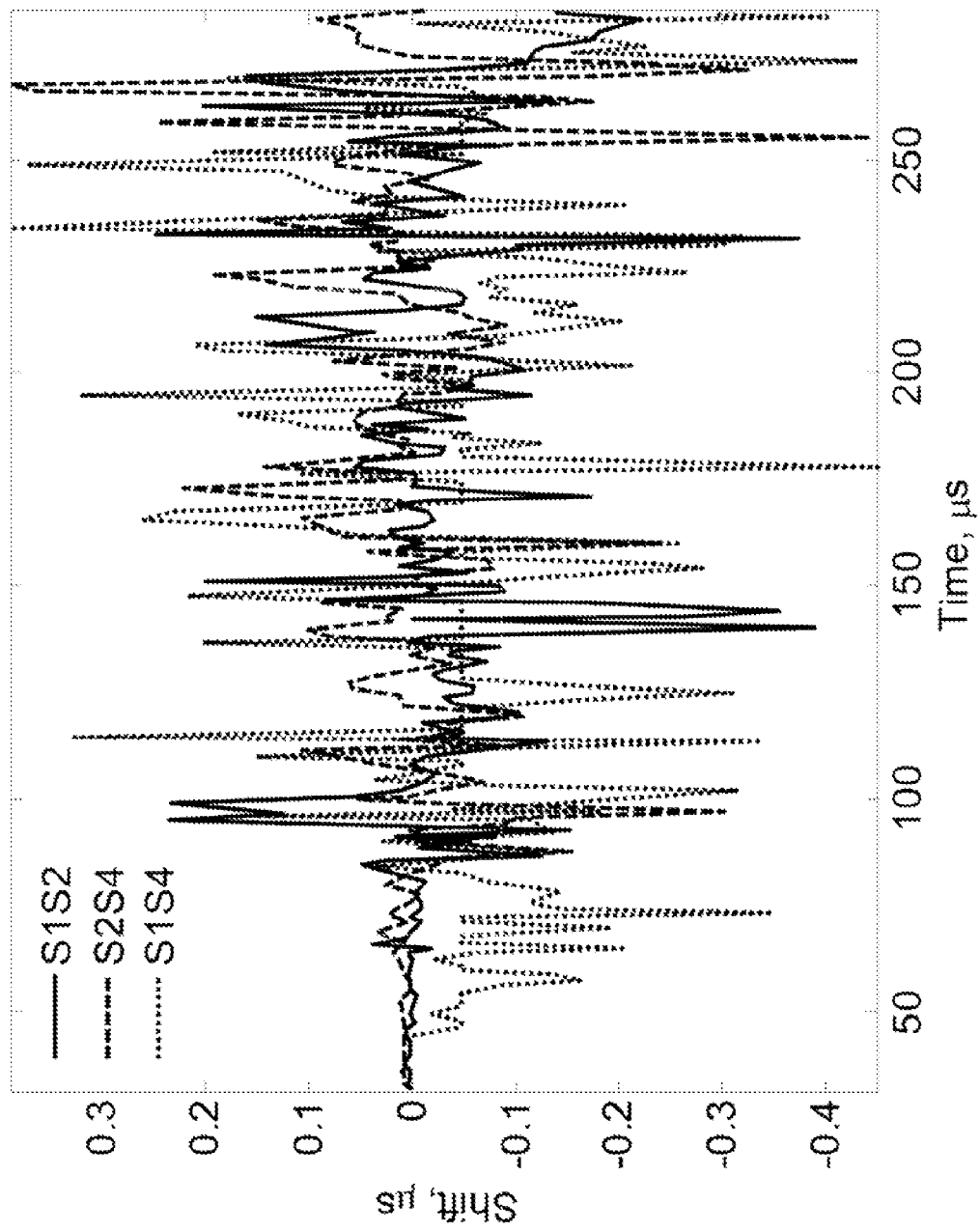
FIGS. 11a & 11b show phase shifts for multiple wave paths in D4 tests, and phase shifts for paths S1S2 and S2S4 respectively.
Figure 11B:
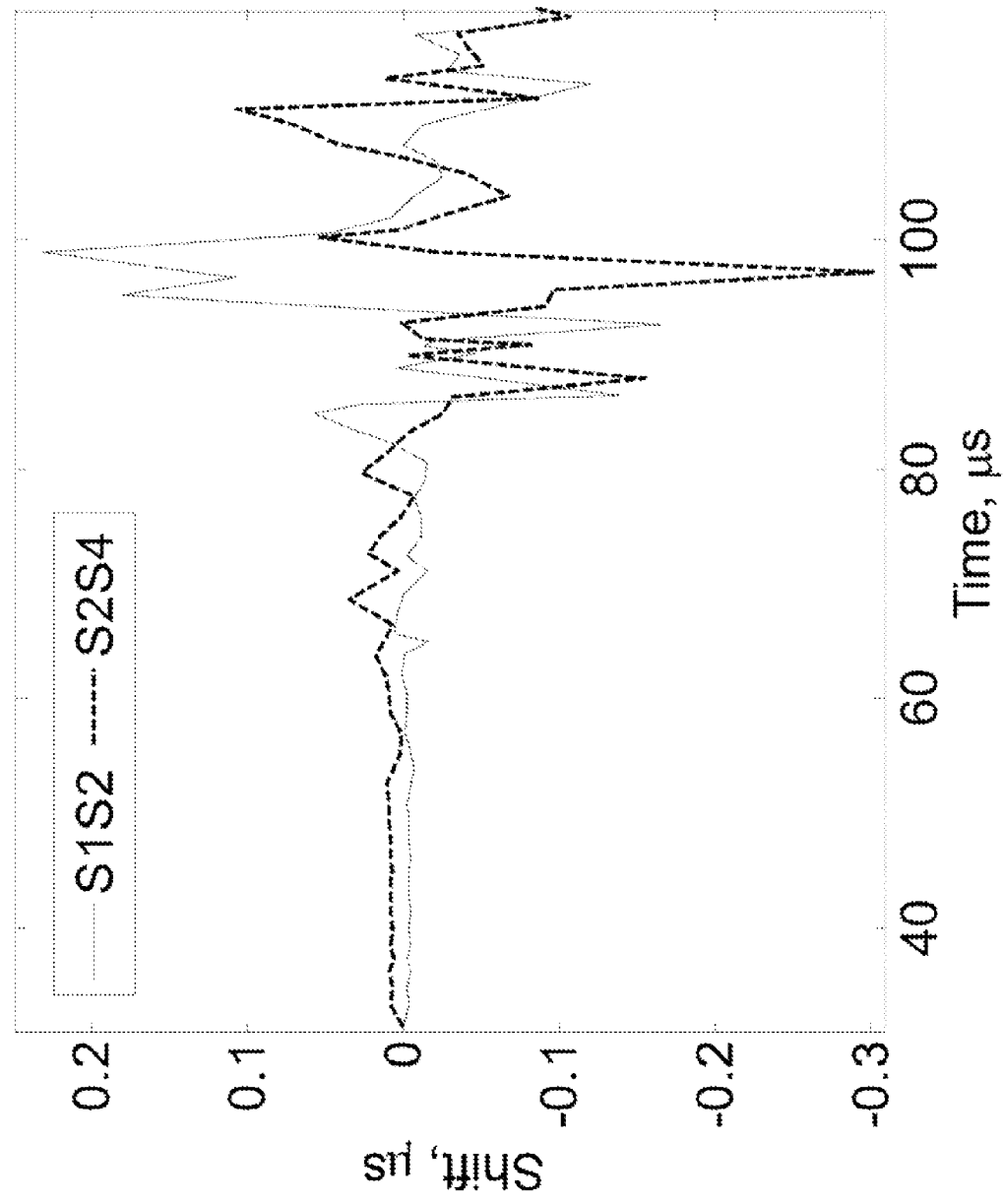

The algorithm used to calculate the phase involved subtracting phases of "tight" and "loose" waveforms. For some areas, where the waveform local maximum was near the zero line additional zero points might emerge in one of the signals, therefore resulting in misinterpretations. These cases were disregarded by clipping them at "O". FIG. 11a shows phase shifts results for all three paths of interest for a loosened bolt D4. The first noticeable characteristic is that the path S1S4, which travels through the loose bolt, experiences almost instantaneous phase shift. This record does not start at the same point as the other records due to the slightly longer distance of the wave propagation. Likewise, paths S1S2 arid S2S4, which were symmetrical with respect to the loosened bolt, manifested phase shift at the same time. (FIG. 11b).

Figure 12:
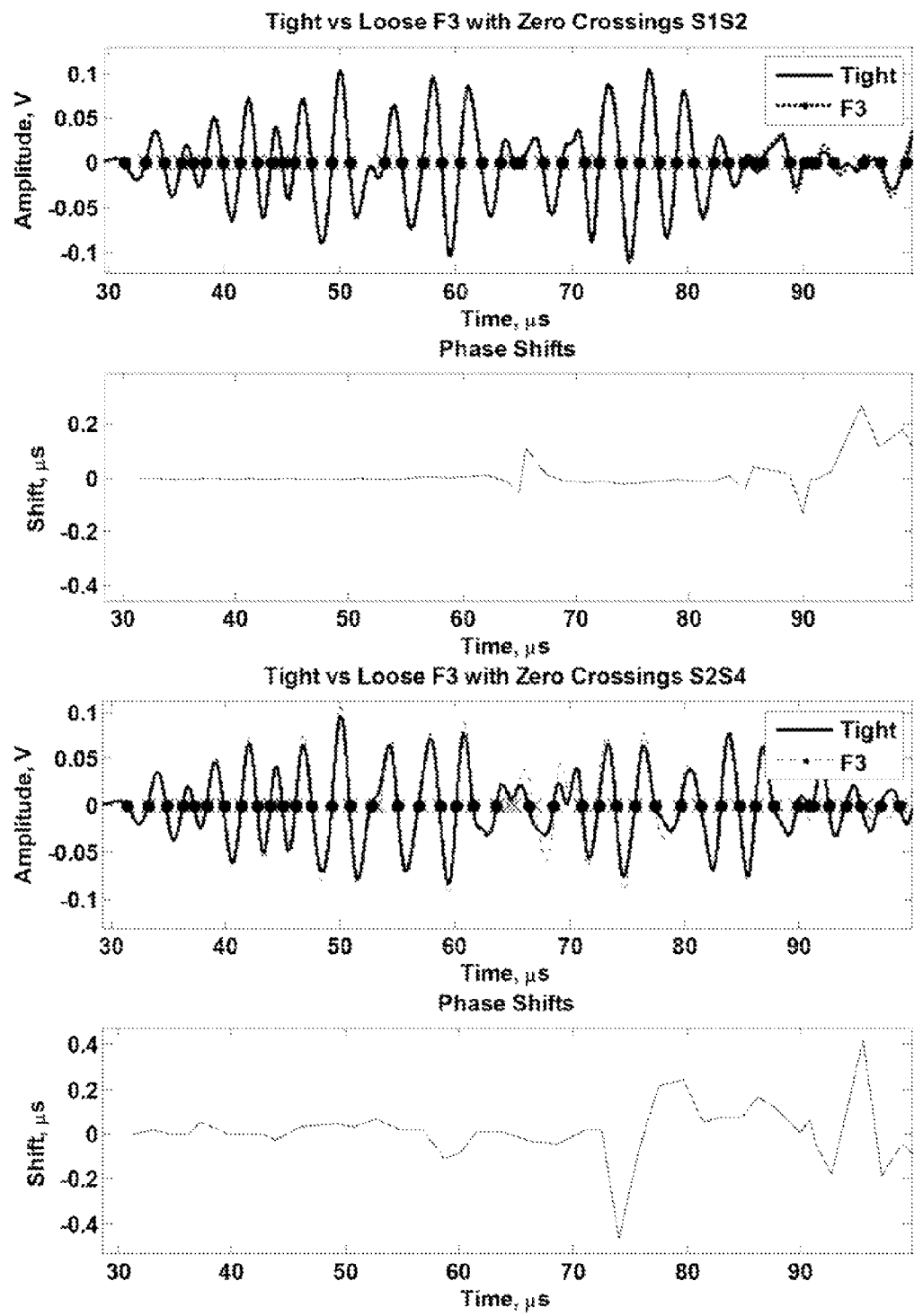
FIG. 12 shows signal records and zero crossing shifts of paths S1S2 and S2S4 for damaged bolt F3.

When results for loose bolt F3 are compared to a tight scenario, FIG. 12 shows that phase shift occurs almost immediately for path S2S4. In this case, the bolt lies near the wave propagation path as compared to path S1S2, where the signal has to be reflected back to sensor S2 to record the shift. This shows that using only two or three of the twelve possible paths it is possible to obtain a realistic estimate of the location of damage.

Figure 13:
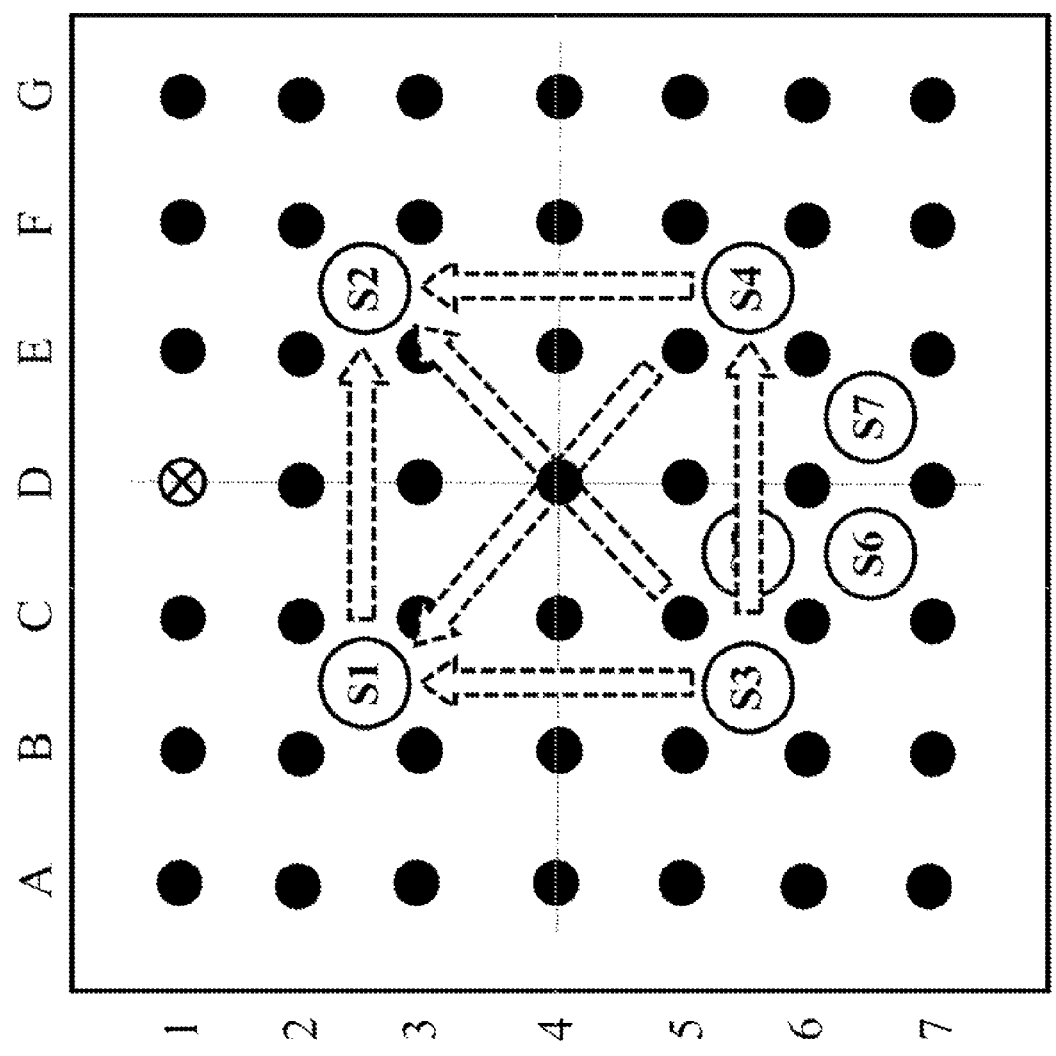
FIG. 13 shows bolt damage location and six paths of interest in a further experiment.

In the final study, all six paths were considered, excluding their reverse transmissions, and a bolt was loosened outside the sensor network, which would correspond to one of the worse-case scenarios. Since bolts near the edge of the panel typically have the lowest effect on phase change, bolt DI was chosen. A schematic of the experiment is indicated in FIG. 13. The three count 325 kHz pulse from the previous test was still being used to excite sensors. Path directions were selected based on maximum attenuation to verify effective range of the sensor network. Six records were obtained for a tight scenario, and then bolt DI was loosened ⅛ of a turn. Since previous tests were done for full turn loose conditions, it was interesting to consider a minimum damage scenario. The resulting phase shifts from the six "tight"–"loose" differences is shown in FIG. 14.

Figure 14:
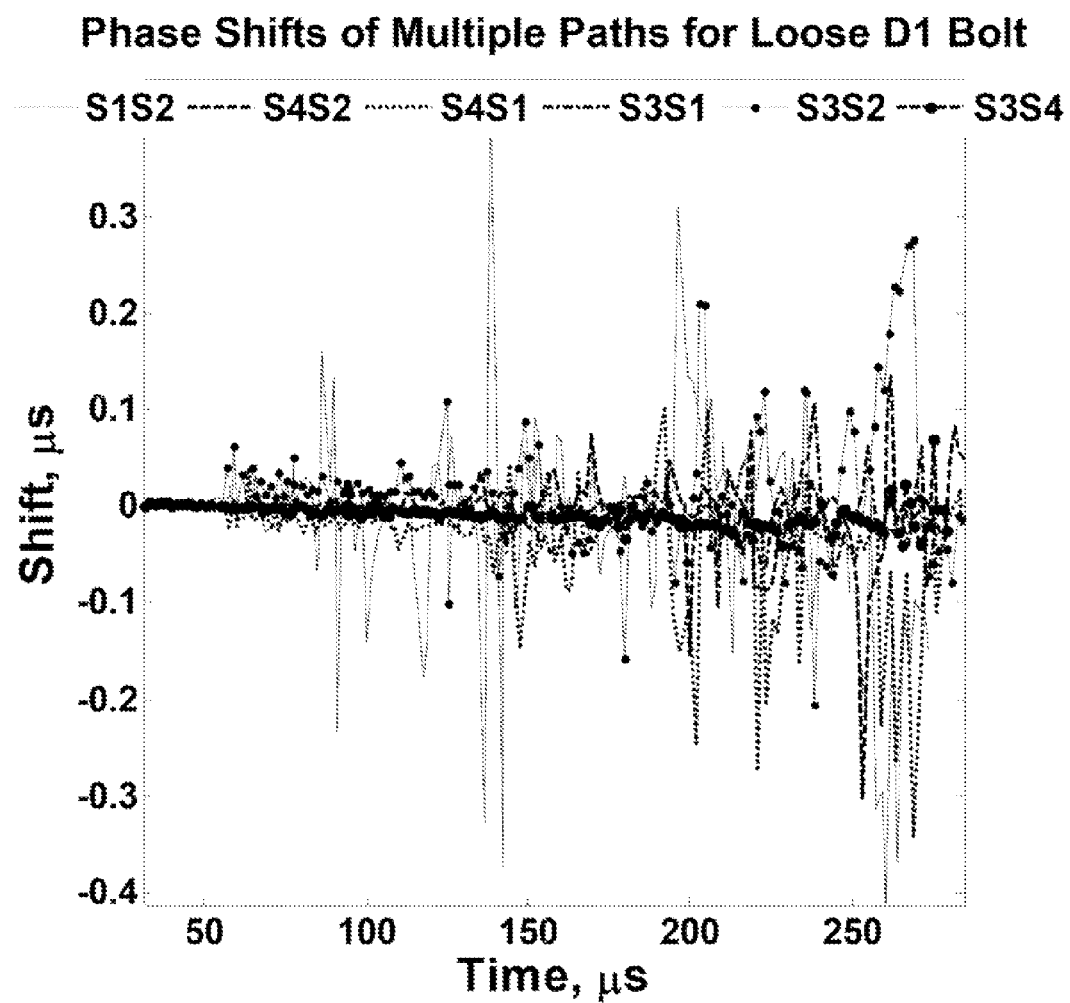
FIG. 14 shows phase shifts for the six paths of interest.

The first observation from FIG. 14 is that the record for S1S2 has the largest shifts (maximum delay of 0.4 µs). Likewise, the shift seen for the S3 S4 path is negligible with a maximum peak of less than 0.1 µs. This leads to the possibility of inferring damage location strictly based on the overall quantity of a shift. Therefore the amount of shift is quantified for each record and normalized to the path with the highest amount of shift and evaluated based on the ratio of each path to that of the highest shift. This is summarized in Table 2.

TABLE 2

Shift ratios based on the path showing greatest change, S1S2

| S1S2 | S4S1 | S3S2 | S4S2 | S3S1 | S3S4 |
|---|---|---|---|---|---|
| 1.0000 | 0.6844 | 0.6806 | 0.3476 | 0.2466 | 0.1736 |

Since the quantity of the shift is related to the path, this feature can be added into predicting damage location. By considering available wave propagation paths, it is possible to isolate the damaged region. Likewise if we consider simply a certain threshold for a shift and set up a radius for each sensor based on the time at which that threshold occurs, the damaged area can be further specified. By assuming a threshold shift of 10e-8 seconds we obtain the time of occurrence for phase change as indicated in Table 3.

TABLE 3

Threshold limit pass times for six paths

| S1S2 | S4S1 | S3S2 | S4S2 | S3S1 | S3S4 |
|---|---|---|---|---|---|
| 9e-5 s | 14.5e-5 s | 12.5e-5 s | 20e-5 s | 20.8e-5 s | N/A |

If the guided waves are considered propagating with a sound speed of approximately 3100 m/s, which would closely correspond to the Rayleigh wave speed, we obtain the following wave path distances hi Table 4.

TABLE 4

Possible wave path distance based on Table 4 times and the guided wave speed at 325 kHz

| S1S2 | S4S1 | S3S2 | S4S2 | S3S1 | S3S4 |
|---|---|---|---|---|---|
| 11 in | 17.7 in | 15.25 in | 24.4 in | 25.4 in | N/A |

Figure 15:
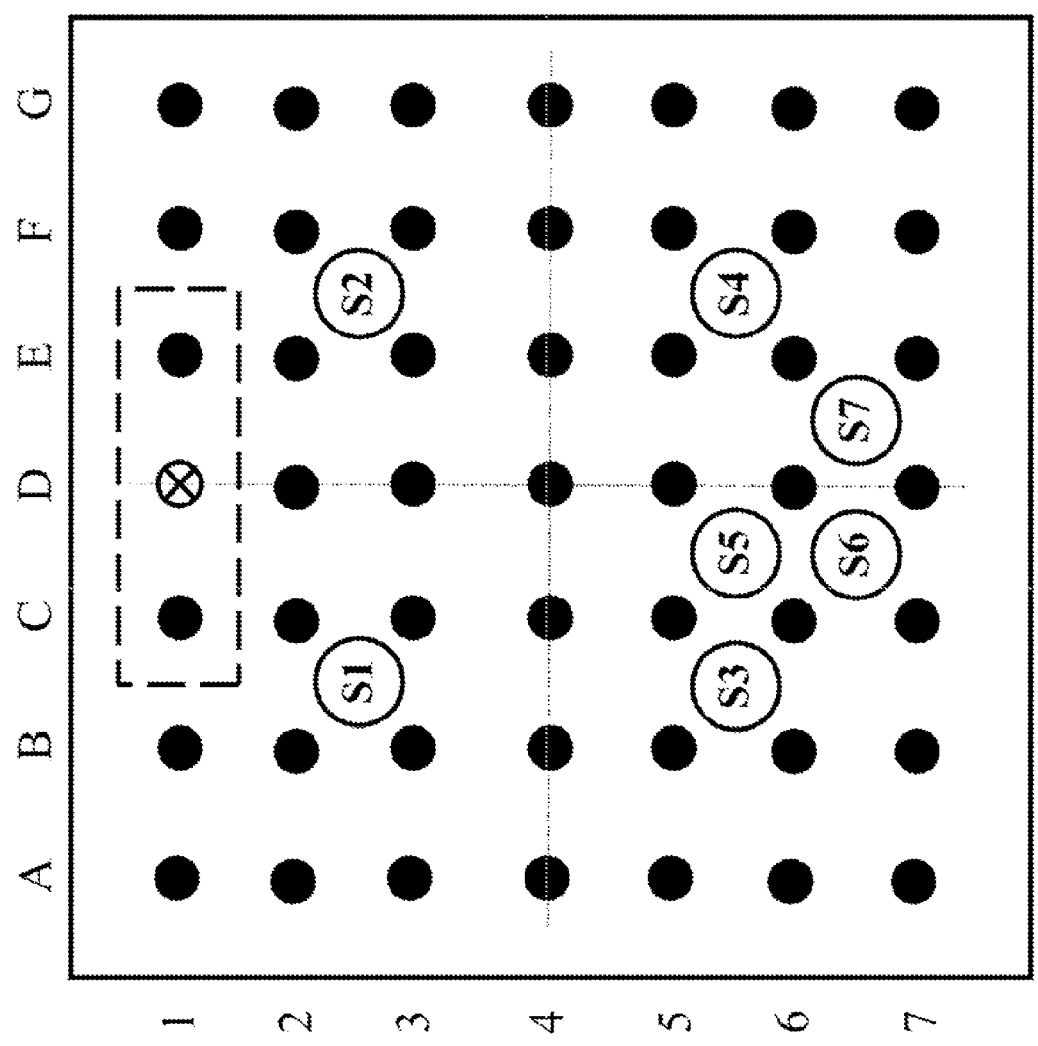
FIG. 15 shows potential loose bolt locations based on distances indicated in Table 4.

Values in Table 4 are approximate, but they do give an estimate on where to look for a loose bolt. If we include a +/−1 inch error margin we can isolate the bolts of importance to the final areas illustrated in FIG. 15, where the highlighted bolts are the ones that fit a path distance.

It should be noted that even performing these estimates by hand calculations yielded exceptional results. It is anticipated that such simple calculations would allow a technician to isolate the area of interest to a few bolts.

For effective measurements, the acousto-elastic method requires an elastic wave record of the intact (undamaged) condition of the joint. Additional studies on the acousto-elastic method were aimed at mitigating the requirement of the "undamaged" baseline. The idea of a baseline-free method comprises making a relative measurement of the current condition of the bolted joint. Two approaches were considered: phase scanning and amplitude scanning. Details of the first method are presented next.

Figure 16:
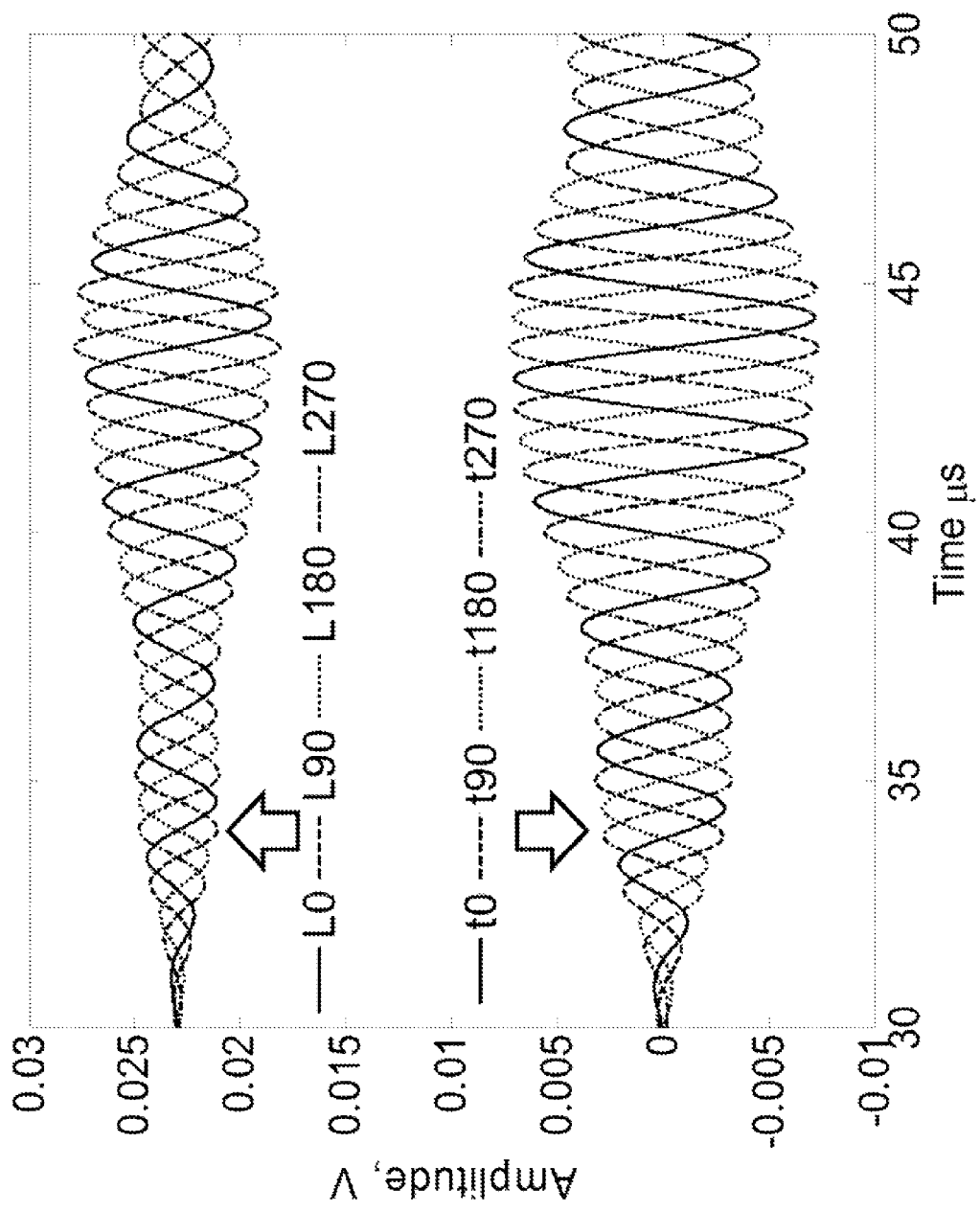
FIG. 16 shows elastic wave signals collected on a bolted plate specimen under "tight" and "loose" conditions of one of the bolts in the joint, with each group of records comprising signals having four different initial phases.
Figure 17:
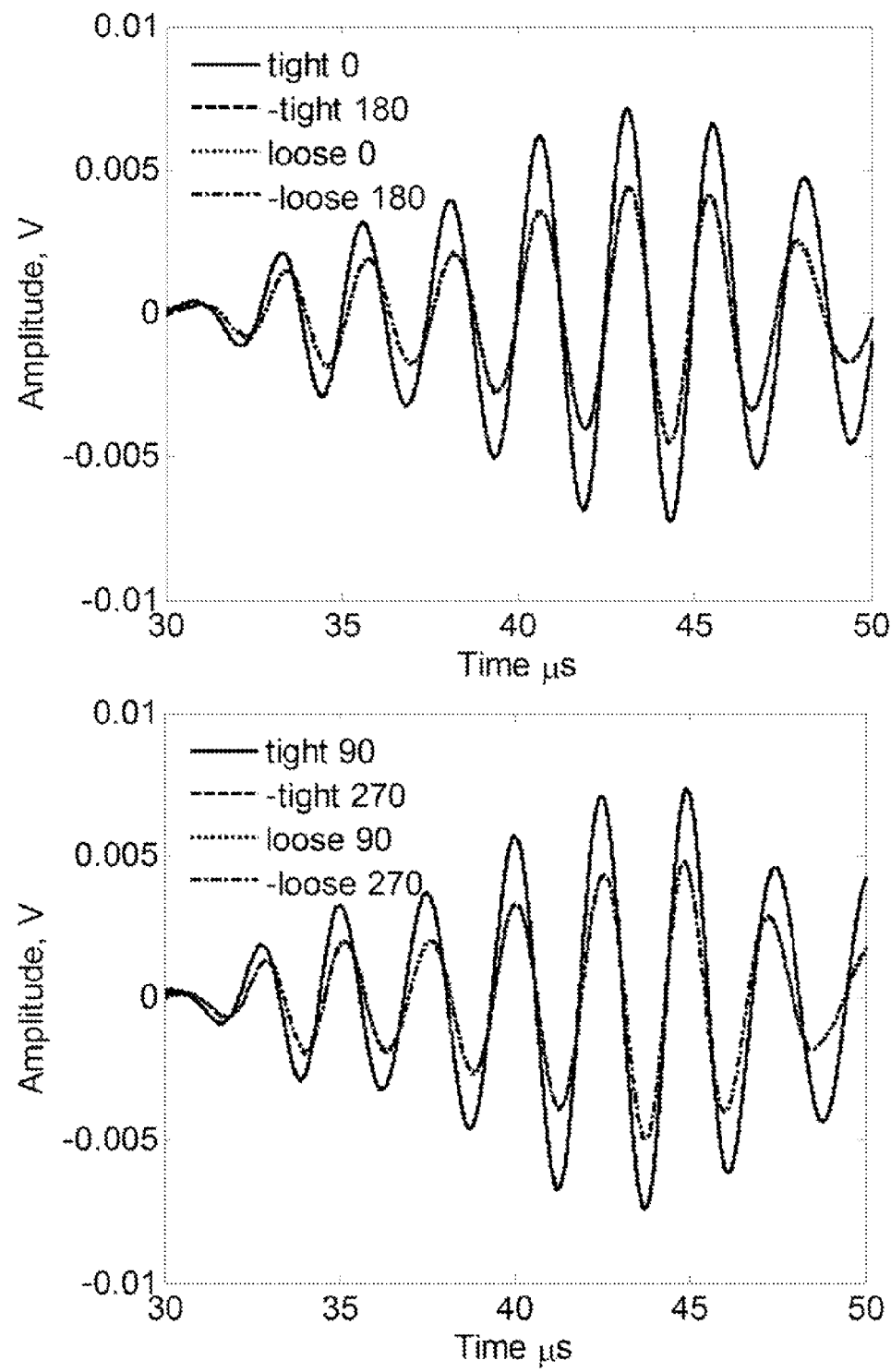
FIG. 17 shows elastic wave signals collected on a bolted plate specimen under "tight" and "loose" conditions of one of the bolts in the joint, with each figure indicating processing of 180 degrees out-of-phase signals.

The phase-scan method employs four identical excitation signals with initial phases shifted by 90 degrees. In the laboratory study, each condition of the bolted joint was assessed with 5 count pulses of 0, 90, 180, and 270 degrees of initial phase. An effect of phase shifting on the received signal is illustrated in FIG. 16, where interference due to transmitted pulse shows phase change of 90 degrees. FIG. 16 was obtained for "loose" and "tight" condition of a single bolt in a bolted joint connecting two thin aluminum plates. All other bolts in the joints were in "tight" condition. FIG. 16 visually indicates differences between signals corresponding to these two conditions; clearly, using one of the signals (e.g. "tight") as a baseline makes discrimination possible. However, in this study, the focus is not on discrimination based on a baseline "tight" condition. In the baseline-free phase-scan method, signals with different initial phases for one condition are compared. It is anticipated that the "damaged" case could introduce more difference to signals of different phase than the "tight" joint. To infer US difference, pairs of 180 degrees out-of-phase signals are compared by introducing a negative, sign in front of one signal in a pair (result of this operation is presented in FIG. 17), and then by subtracting the negative signal.

Figure 18:
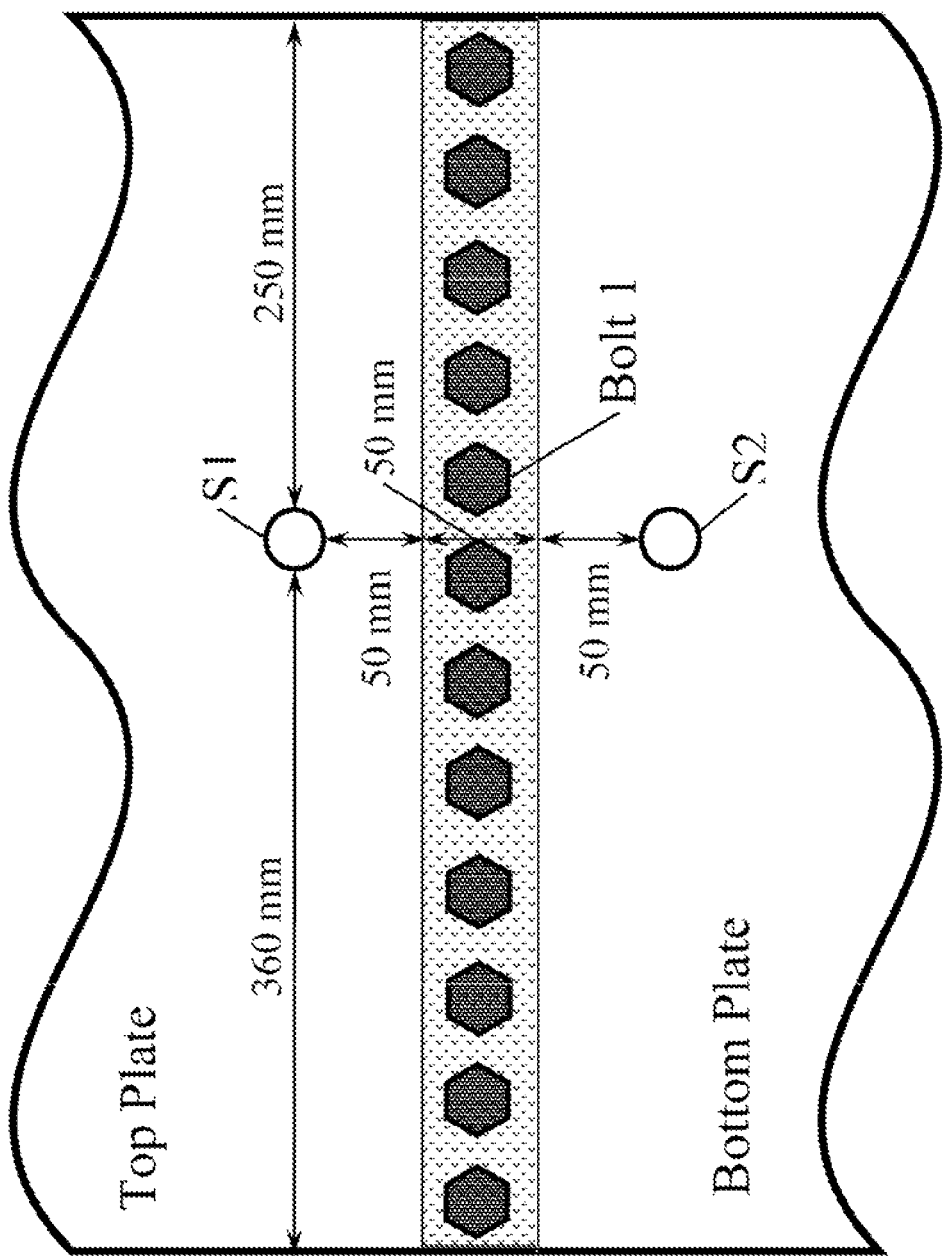
FIG. 18 shows a bolted plate specimen utilized in proof-of concept phase scan measurements.

In the proof-of-concept experiment, all bolts in the joint were subjected to 50 fl-lbs torque. One bolt, directly on a line (left) between sensors S2 and S1 (FIG. 18) was subjected to "finger-tight" representing "loose" condition and 35 lbs-ft representing "tight" condition. Sensor S2 was utilized as a transmitter and sensor S1 as a receiver of elastic wave signals with different initial phases. An excitation signal was a 5 count pulse with a central frequency of 400 kHz. As a result, 4 signals (0, 90, 180, and 270 degrees) were obtained for each load condition.

Figure 19A:
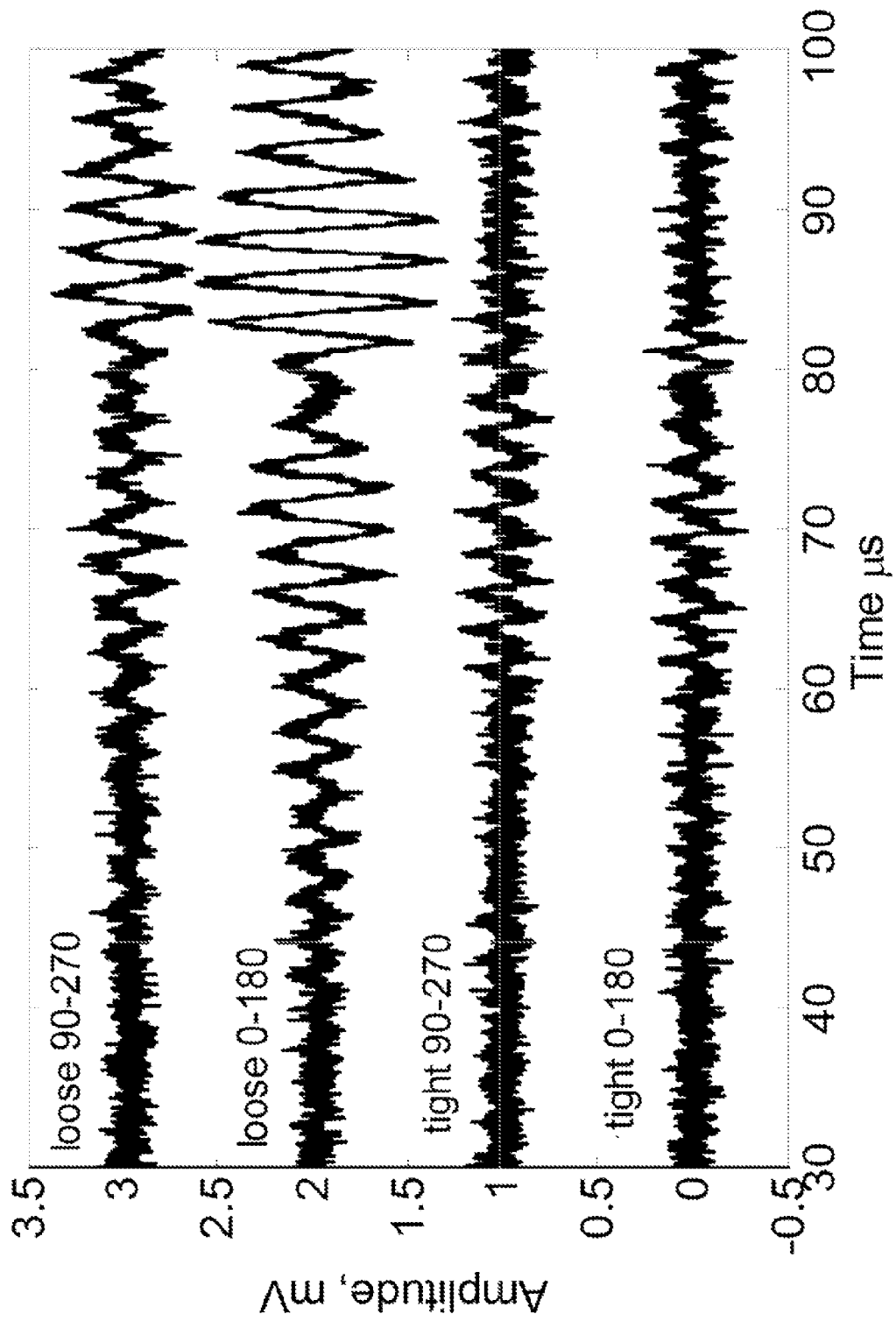
FIG. 19a shows results of subtraction of out-of-phase signals for different stress conditions in a bolted joint, with "tight" being the data for 35 ft-lbs and "loose" being the data for a "finger-tight" stress condition.
Figure 19B:
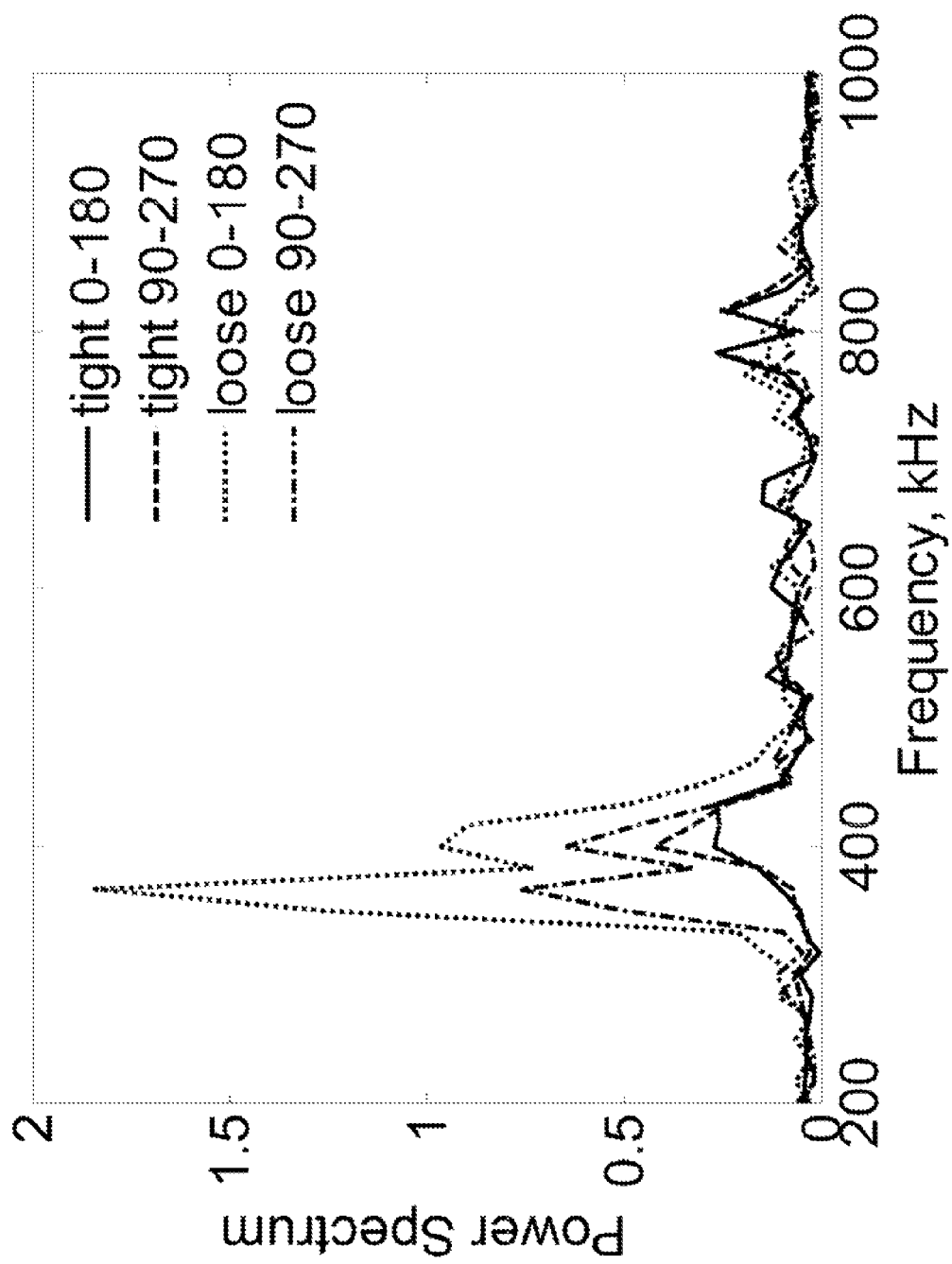

Results of subtraction of signals with 0 and 180 degrees and 90 and 270 degrees of initial phase are illustrated in FIG. 19a. As can be seen in FIG. 19a, the "finger tight" condition shows much larger amplitude of the out-of-phase signals. To quantify difference in amplitude of these signals, their spectral characteristics (using FFT) were calculated as shown in FIG. 19b. An advantage of using spectral characteristics is that such characteristics provide amplitude of spectral component at transmitted frequency of 400 kHz and, in addition, show evolution of spectrum due to different stress conditions. The latter may be considered as an addition parameter in discriminating torque levels.

An algorithm for baseline-free, detection of a defective joint could incorporate assessment using a threshold. For example, a threshold in the proof-of-concept experiments may be set to 0.5 amplitude of the spectrum in FIG. 19b. The "finger-tight" (i.e. loose bolt) case is reliably distinguished from the "tight" 35 ft-lbs condition. Proof-of-concept experiments have shown capability of the baseline-free amplitude scan method to detect the "loose bolt" condition. This approach may also be used to discriminate torque levels.

Figure 20A:
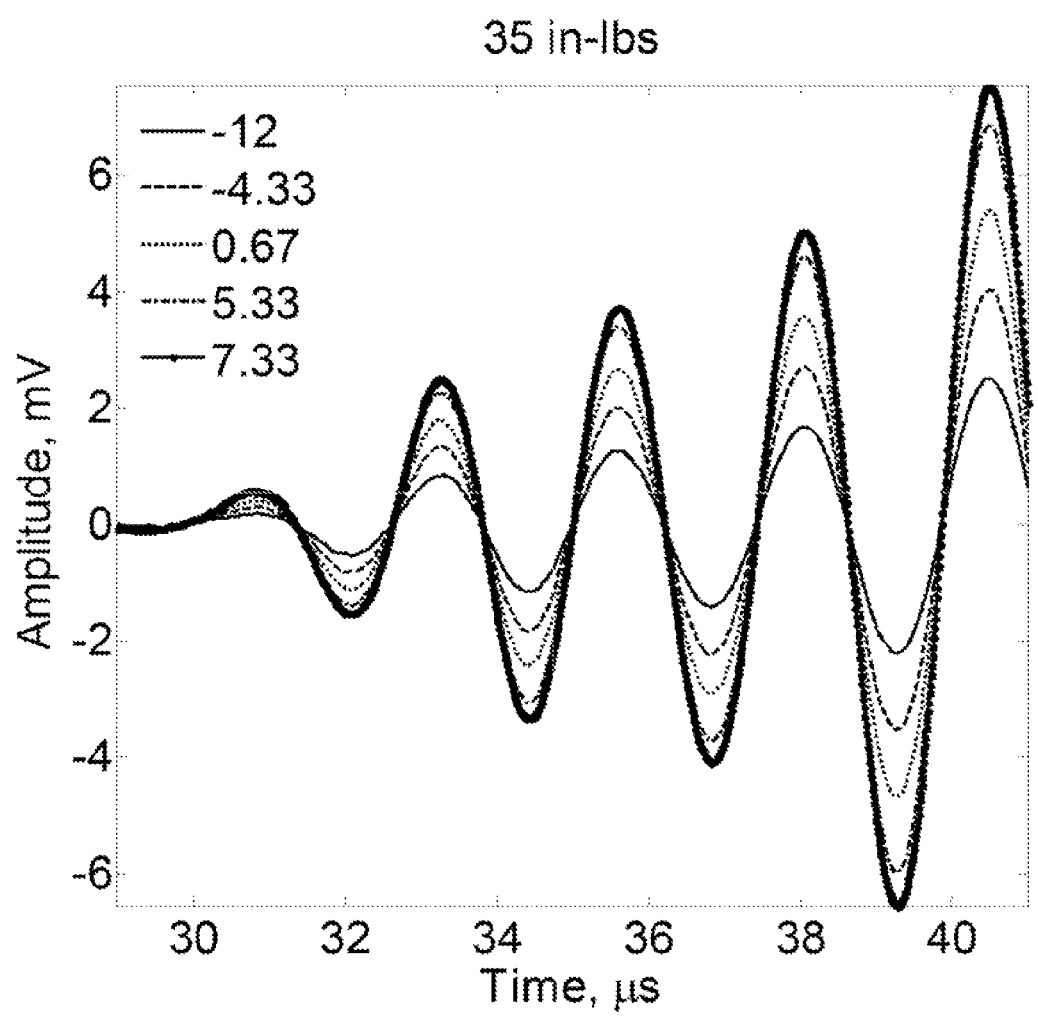
FIG. 20a shows the acousto-elastic response of a bolted joint at increasing amplitude of a transmitted acoustic signal.
Figure 20B:
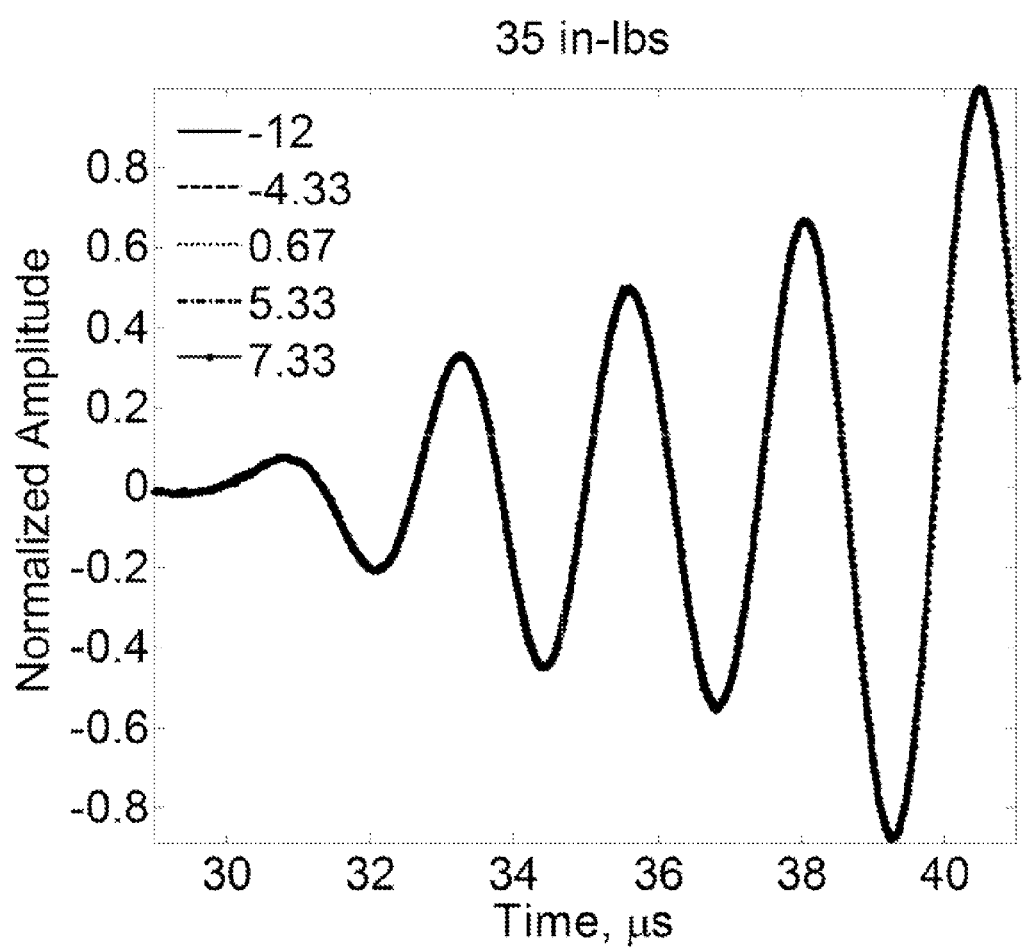
FIG. 20b shows normalized acousto-elastic responses.

Acousto-elasticity is a nonlinear effect manifested through nonlinearity of the stress-strain relationship. As with many other nonlinear phenomena, it depends on stress amplitude: the larger the stress, the more pronounced are changes in nonlinear response noticeable. This feature is explored in the baseline-free acousto-elastic amplitude scan method, where an acousto-elastic response is measured at increasing amplitudes of transmitted signal (FIG. 20a). Larger amplitudes cause larger phase shifts. Hence, relative change of the phase shift from an initial level may be used to assess stress condition in the bolted joint. Signal processing for the amplitude-scan method comprises normalizing acousto-elastic responses measured at increasing amplitudes of transmitted signal (FIG. 20b) and calculating relative phase shifts.

Figure 21A:
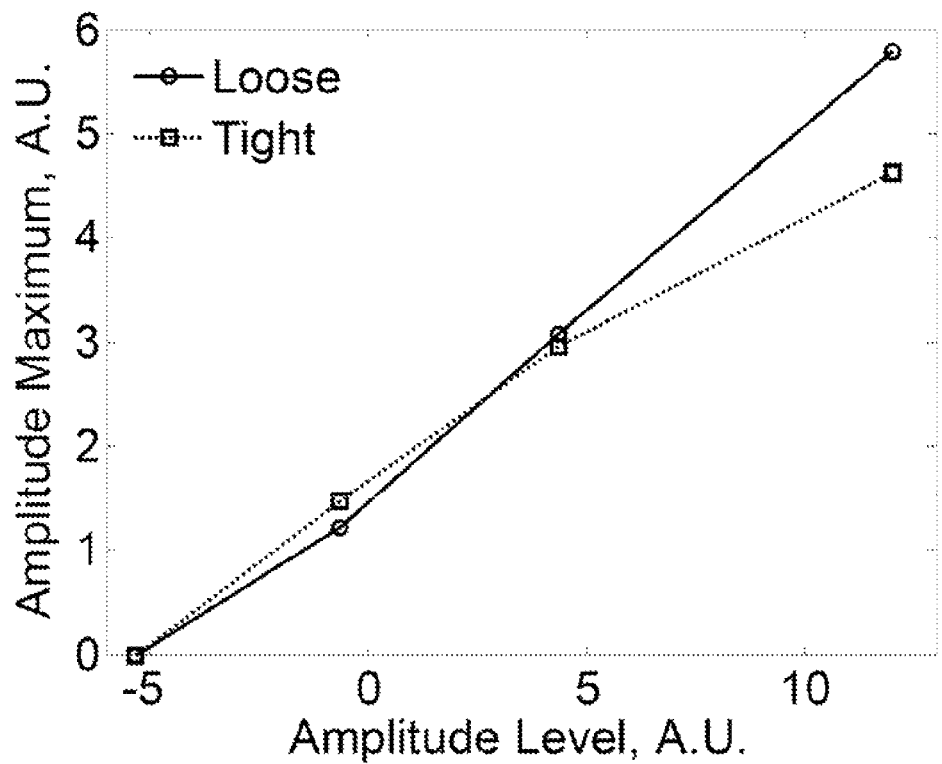
FIG. 21a shows maximum signal amplitude inferred from difference of signals at multiple amplitude levels.
Figure 21B:
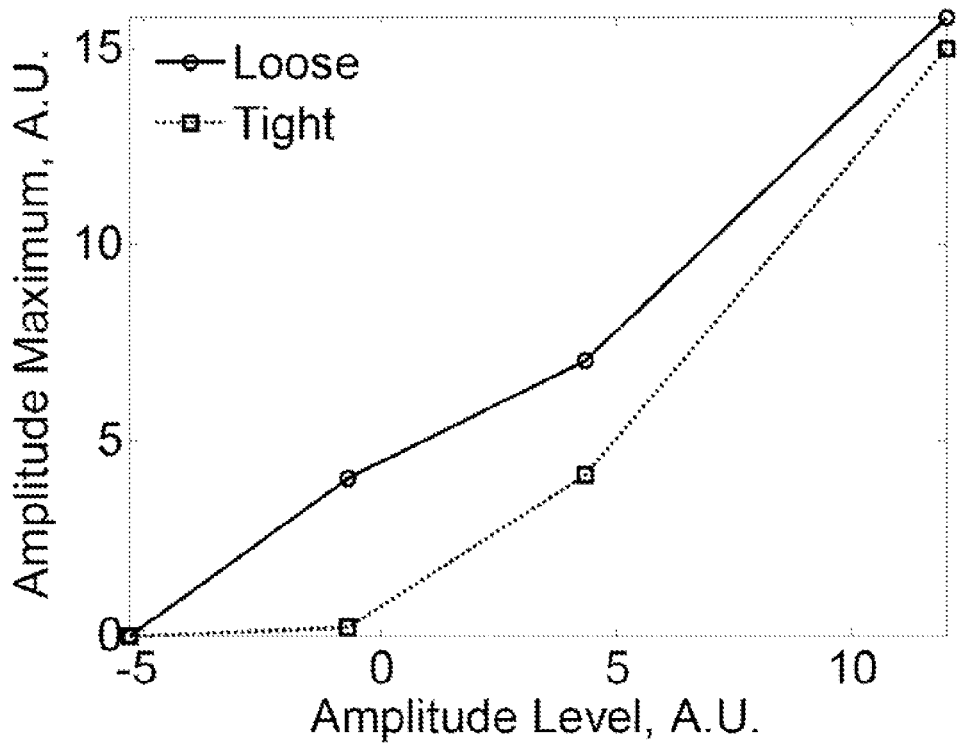
FIG. 21b shows maximum spectral amplitude inferred from difference of signals at multiple amplitude levels.

To infer the magnitude of the phase shift, signals measured at various levels of transmitted signal are subtracted from the time-domain record of the signal of maximum amplitude (this is done to improve signal-to-noise characteristics). Amplitude of the difference signal is proportional to the phase shift and can be measured either directly from the time-domain record or by calculating the power spectrum and considering amplitude of the fundamental spectral component. The first approach is illustrated in FIG. 21a and the second approach is illustrated in FIG. 21b for the "loose" and "tight" condition of one bolt in the previously described (FIG. 18) bolted joint. FIG. 21 shows that the amplitude scan baseline-free method can be used to differentiate condition of the bolted joint based on behavior of the curve. This method may be also utilized to discriminate the torque levels.

Figure 22:
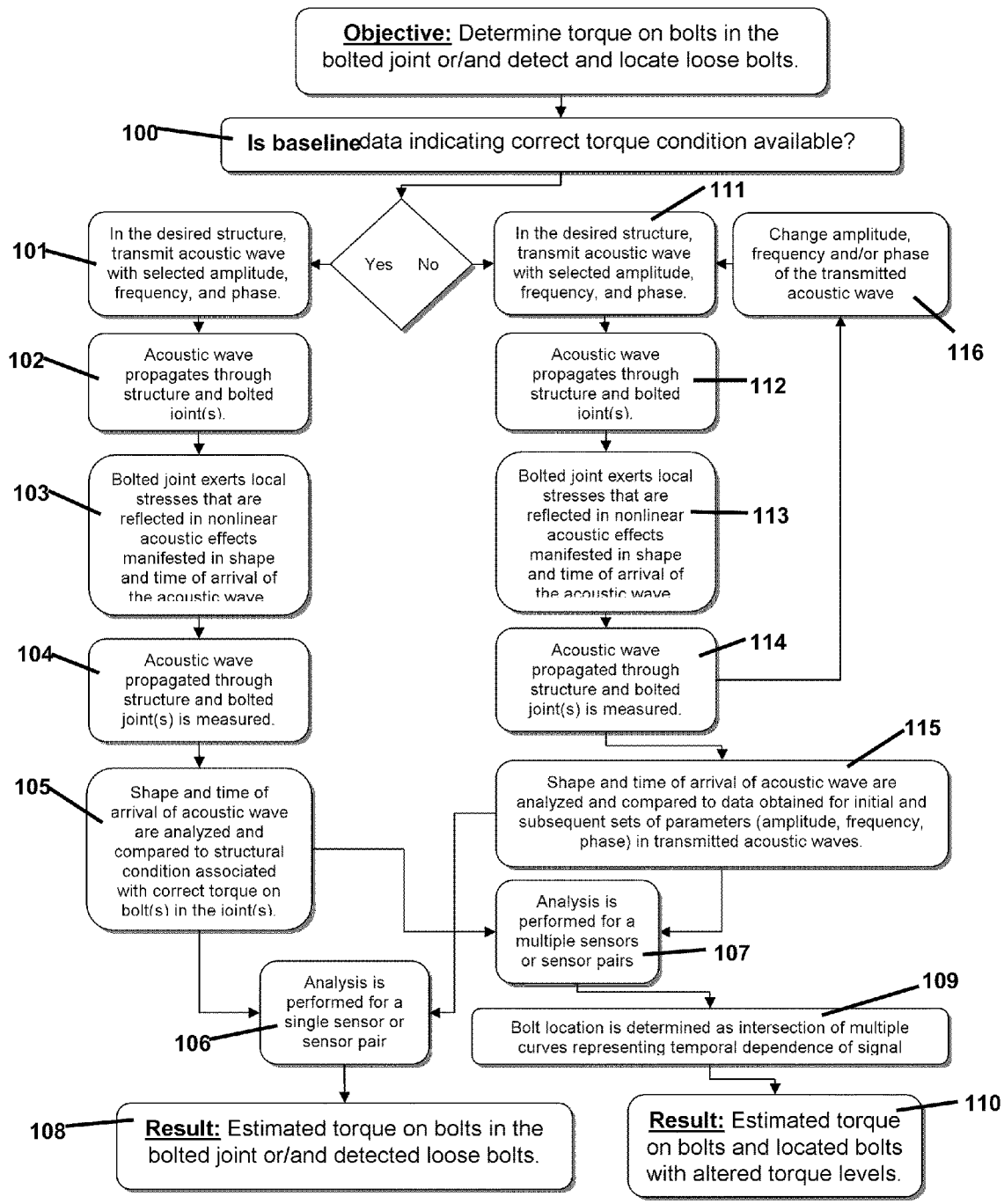
FIG. 22 is a flowchart depicting the termination of torque on bolts in a bolted joint assembly, and/or the detection and location of loose bolts, depending on whether or not baseline data indicating correct torque condition is available.

The objective of applicants' method of assessing bolted joint integrity, in particular determining torque on bolts in the bolted joint, and/or detecting and locating loose bolts, is summarized in the flowchart of FIG. 22. In particular, the two aforementioned alternatives are provided, depending on whether or not baseline data indicating correct torque condition is available (block 100). If the answer is Yes, then one proceeds to block 101, where in the structure being evaluated, an acoustic wave having selected amplitude, frequency and/or phase is transmitted. The acoustic wave then propagates through the structure 10 (FIG. 1) and the bolted joint assembly (block 102). As indicated in block 103, the bolted joint exerts local stresses that are reflected in nonlinear acoustic effects, which are manifested in the shape and time of arrival of the acoustic wave. Thereupon, in block 104, the acoustic wave propagated through the structure and the bolted joint assembly is measured. Subsequently, the shape and time of arrival of the acoustic wave are analyzed and compared to structural conditions associated with the correct torque on the bolt or bolts in the bolted joint assembly (block 105). The analysis indicated in block 105 can be performed either for a single sensor or sensor pair (block 106), or for multiple sensors or sensor pairs (block 107). If the analysis is performed for a single sensor or sensor pair, then the result obtained is the estimated torque on the bolt or bolts of the bolted joint assembly and/or a loose bolt or bolts are detected (block 108). On the other hand, if analysis is performed for multiple sensors or sensor pairs (block 107), then bolt location is determined as an intersection of multiple curves representing temporal dependence of signal (block 109), with the result obtained being the estimated torque on the bolt or bolts and the location of a bolt or bolts having altered torque levels (block 110).

Returning to block 100, if the answer to the question of whether or not baseline data indicating correct torque condition available is No, then in the structure 10 (FIG. 1) being investigated, an acoustic wave having selected amplitude, frequency and/or phase is transmitted (block 111). Again, the acoustic wave propagates through the structure and the bolted joint assembly (block 112). As indicated in block 113, the bolted joint exerts local stresses that are reflected in nonlinear acoustic effects, which are manifested in the shape and time of arrival of the acoustic wave. In block 114, the acoustic wave propagated through the structure and the bolted joint assembly is measured. In block 115, the shape and time of arrival of acoustic waves are analyzed and compared to data obtained for initial and subsequent sets of parameters, i.e. amplitude, frequency and/or phase, in the transmitted acoustic wave or waves. Again, analysis can be performed for either a single sensor or sensor pair (block 106), or for multiple sensors or sensor pairs (block 107). As discussed above, depending on whether the analysis is performed on a single sensor or sensor pair, or for multiple sensors or sensor pairs, the results reflected in blocks 108 or 110 respectively will be obtained.

In order to measure a sequence of guided waves, the amplitude, frequency and/or phase of transmitted acoustic waves is changed (see block 116), and the steps reflected in blocks 111 through 114 are repeated. The change of amplitude, frequency and/or phase of the transmitted acoustic wave (block 116) must be changed at least once, and preferably four or eight times.

The specification incorporates by reference the disclosure of U.S. priority document, U.S. provisional application 61/286,248 filed Dec. 14, 2009.

The present invention is, of course, in no way restricted to the specific disclosure of the specification and drawings, but also encompasses any modifications within the scope of the appended claims.

What I claim is:

1. A method of assessing bolted joint integrity, including the steps of:
   sending a guided wave through a structure that contains at least one bolted joint, which is at a given torque;
   measuring the guided wave that has subsequently propagated through the structure and interacted with said at least one bolted joint, thus obtaining a measured result at a level of said torque of said bolted joint;
   analyzing and storing the value of at least one parameter of the measured result of the guided wave after its travel through the structure and after having been affected by a nonlinear acoustic behavior of said at least one bolted joint;
   assessing joint integrity of said at least one bolted joint by sending a further guided wave through said structure and obtaining a second measured result at the level of said torque of said bolted joint, and then either comparing the value of at least one guided wave parameter of said second measured result to said stored value, or comparing values of at least one guided wave parameter measured for a plurality of bolted joints, to determine changes in at least one of wave propagation time and wave propagation shape; and
   indicating from any changes that are determined the integrity of said at least one bolted joint.

2. A method according to claim 1, which includes the further step of considering the time of occurrence of changes in at least one of wave propagation time and wave propagation shape to locate a bolted joint having an incorrect torque level.

3. A method according to claim 1, wherein said step of sending a guided wave comprises sending a guided wave having a predefined sequence of at least one of amplitude, frequency and phases through the structure.

4. A method according to claim 3, wherein said measuring step comprises measuring the sequence of the guided waves.

5. A method according to claim 4, wherein said analyzing step comprises analyzing at least one parameter of the guided wave sequence.

6. A method according to claim 5, wherein said comparing values step comprises comparing values of at least one guided wave parameter, at least one of which is related to wave propagation time and wave propagation shape, in a sequence to evaluate torque in said at least one bolted joint, and wherein said indicating step comprises indicating an incorrect torque level of said at least one bolted joint from any variation that is determined.

7. A method according to claim 6, which includes the further step of considering the time of occurrence of a variation of at least one guided wave parameter to locate a bolted joint having an incorrect torque level.

8. A method according to claim 4, wherein said step of measuring comprises measuring at least two guided waves, each of which has a different sequence of at least one of amplitude, frequency and phase.

9. A method according to claim 8, wherein four or eight guided waves having a differing sequence of at least one of amplitude, frequency and phase are measured.

* * * * *